US009895322B2

(12) United States Patent
Singh et al.

(10) Patent No.: US 9,895,322 B2
(45) Date of Patent: Feb. 20, 2018

(54) PHARMACEUTICAL COMPOSITIONS FOR THE DELIVERY OF SUBSTANTIALLY WATER-INSOLUBLE DRUGS

(71) Applicants: Mewa Singh, Zachary, LA (US);
Maninder Sandhu, Zachary, LA (US)

(72) Inventors: Mewa Singh, Zachary, LA (US);
Maninder Sandhu, Zachary, LA (US)

( * ) Notice: Subject to any disclaimer, the term of this patent is extended or adjusted under 35 U.S.C. 154(b) by 0 days.

(21) Appl. No.: 14/534,400

(22) Filed: Nov. 6, 2014

(65) Prior Publication Data

US 2015/0080353 A1  Mar. 19, 2015

Related U.S. Application Data

(63) Continuation-in-part of application No. PCT/US2013/035792, filed on Apr. 9, 2013.
(Continued)

(51) Int. Cl.
*A61K 31/12* (2006.01)
*A61K 31/337* (2006.01)
(Continued)

(52) U.S. Cl.
CPC ............ *A61K 31/12* (2013.01); *A61K 9/0019* (2013.01); *A61K 9/19* (2013.01); *A61K 9/5138* (2013.01);
(Continued)

(58) Field of Classification Search
CPC ..... A61K 31/337; A61K 31/12; A61K 9/5138
See application file for complete search history.

(56) References Cited

U.S. PATENT DOCUMENTS 5,714,520 A  2/1998  Jones et al.
5,731,355 A  3/1998  Jones et al.
(Continued)

FOREIGN PATENT DOCUMENTS

WO  9939696 A1  8/1999
WO  2012175518 A1  12/2012
(Continued)

OTHER PUBLICATIONS

Acharya et al.; "Sustained targeting of Bcr-Abl + leukemia cells by synergistic action of dual drug loaded nanoparticles and its implication for leukemia therapy"; Biomaterials; May 19, 2011; 32: 5643-5662 & Supplemental information appendix, 1-9.*
(Continued)

*Primary Examiner* — Timothy P Thomas
(74) *Attorney, Agent, or Firm* — Caesar Rivise, PC

(57) ABSTRACT

The subject invention relates to compositions and methods useful for the in vivo delivery of substantially water-insoluble drugs, like taxol. The use of specific composition and preparation conditions enables the reproducible production of unusually water-soluble formulation, which can be sterile-filtered. The particulate system produced according to the invention can be converted into a re-dispersible dry powder comprising nanoparticles of drug. The innovation is also based on the fact that complementary partner is also an active drug but may have a different mode action with respect to primary molecule of the hybrid drug. The complementary molecule has multiple properties like antioxidant, antimicrobial, anti-inflammatory, anti-allergic, cox-2 inhibitors, etc. This results in a unique delivery system, in which part of the pharmacologically active agent is readily bioavailable.

2 Claims, 12 Drawing Sheets

Related U.S. Application Data

(60) Provisional application No. 61/647,727, filed on May 16, 2012.

(51) Int. Cl.
| | |
|---|---|
| *A61K 45/06* | (2006.01) |
| *A61K 31/05* | (2006.01) |
| *A61K 31/135* | (2006.01) |
| *A61K 31/192* | (2006.01) |
| *A61K 31/203* | (2006.01) |
| *A61K 31/341* | (2006.01) |
| *A61K 31/36* | (2006.01) |
| *A61K 31/4745* | (2006.01) |
| *A61K 31/5513* | (2006.01) |
| *A61K 31/616* | (2006.01) |
| *A61K 9/00* | (2006.01) |
| *A61K 9/19* | (2006.01) |
| *A61K 9/51* | (2006.01) |
| *A61K 31/045* | (2006.01) |
| *A61K 31/4375* | (2006.01) |
| *A61K 31/60* | (2006.01) |

(52) U.S. Cl.
CPC .......... *A61K 9/5146* (2013.01); *A61K 9/5161* (2013.01); *A61K 9/5169* (2013.01); *A61K 9/5192* (2013.01); *A61K 31/045* (2013.01); *A61K 31/05* (2013.01); *A61K 31/135* (2013.01); *A61K 31/192* (2013.01); *A61K 31/203* (2013.01); *A61K 31/337* (2013.01); *A61K 31/341* (2013.01); *A61K 31/36* (2013.01); *A61K 31/4375* (2013.01); *A61K 31/4745* (2013.01); *A61K 31/5513* (2013.01); *A61K 31/60* (2013.01); *A61K 31/616* (2013.01); *A61K 45/06* (2013.01)

(56) References Cited

U.S. PATENT DOCUMENTS

| | | | |
|---|---|---|---|
| 5,731,356 A | 3/1998 | Jones et al. | |
| 6,028,108 A | 2/2000 | George | |
| 6,100,302 A | 8/2000 | Pejaver et al. | |
| 6,147,122 A | 11/2000 | Mirejovsky et al. | |
| 6,177,477 B1 | 1/2001 | George et al. | |
| 6,399,087 B1 | 6/2002 | Zhang et al. | |
| 6,469,069 B1 | 10/2002 | Mirejovsky et al. | |
| 6,537,579 B1 | 3/2003 | Desal et al. | |
| 6,730,330 B2 | 5/2004 | Whittle et al. | |
| 8,501,248 B1 | 8/2013 | Sugerman | |
| 2005/0004002 A1 | 1/2005 | Desai et al. | |
| 2011/0028431 A1 | 2/2011 | Zerbe et al. | |
| 2012/0270845 A1 | 10/2012 | Bannister et al. | |

FOREIGN PATENT DOCUMENTS

| | | |
|---|---|---|
| WO | 2013006729 A1 | 1/2013 |
| WO | 2013108254 A1 | 7/2013 |
| WO | 2013172999 A1 | 11/2013 |

OTHER PUBLICATIONS

El-Gendy et al.; "Combination Chemotherapeutic Dry Powder Aerosols via Controlled Nanoparticle Agglomeration"; Pharmaceutical Research; 2009; Pharmaceutical Research; 26(7): 1752-1763.*

Dandekar et al.; "Curcumin-Loaded Hydrogel Nanoparticles: Application in Anti-Malarial Therapy and Toxicological Evaluation"; 2010; Journal of Pharmaceutical Sciences; 99(12): 4992-5010.*

Prajakta P. Dankekar, et al, Curcumin-Loaded Hydrogel Nanoparticles: Applicaito in Anti-Malarial Therapy and Toxicological Evaluation, Journal of Pharmaceutical Sciences, vol. 99, No. Dec. 2010 4992-5010.

Nashwa El-Gendy, et al., Combination Chemotherapeutic Dry Powder Aerosols via Controlled Nanoparticle Agglomeration, Pharmaceutical Rsearch, vol. 26, No. 7, Jul. 2009 1752-1763.

Sarbari Acharya, et al., Sustained targeting of Bcr-Abl+leukemia cells by synergistic action of dual drug loaded nanoparticles and its implication for leukemia therapy, Biomaterials 32 (2011) 5643-5662.

Mou-Tuan Huang, et al, Inhibitory Effect of Curcumin, Chlorogenic Acid, and Ferulic Acid on Tumor Promotion in Mouse Skin by 12-)-Tetradecanoylphorbol-13-acetate, Cancer Research 48, 5941-5946, Nov. 1, 1988.

Reimann, et al., Histamine Release in Dogs by Cremophor EI and its Derivatives: Oxethylated Oleic Acid is the Most Effective Constituent, Agents and Actions vol. 7/1 (1977) 63-67.

Hasmeda, et al., Inhibition of Cyclic Amp-Dependent protein Kinase by Curcumin, Phytochemistry, vol. 42, No. 3, pp. 599-605, 1996.

Anto, et al., Antimutagenic and anticarcinogenic activity of natural and synthetic curcuminoids, Mutuation Research 370 (1996) 127-131.

Reddy, et al., Curcumin is a non-competitive and selective inhibitor of phosphorylase kinase, FEBS Letters 341 (1994) 19-22.

Osawa, et al., Antioxidative Activity of Tetrahydrocurcuminoids, Biosci. Biotech. Biochem., 59 (9), 1609-1612, 1995.

International Search Report and Written Opinion of Application No. PCT/US15/28718 dated Jul. 24, 2015.

* cited by examiner

Figure 1
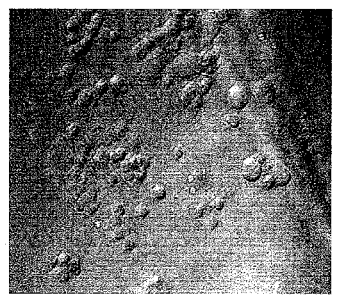
Paclitaxel
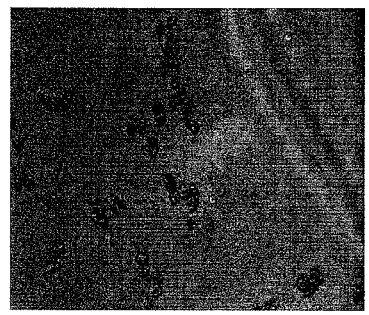
Soluble Paclitaxel
Cytotoxic activity
Solubility : microscopic images of the Paclitexel and water soluble Paclitexel formulation
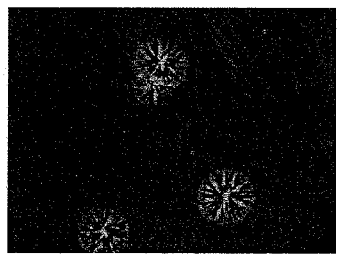
Paclitaxel Crystals
Paclitaxel in growth medium
Water soluble Paclitaxel

Wavelength Scan - Scanning    Figure 2          Print Date: May 07, 2012 10:02 AM

```
Instrument Name       : DU 800 Spectrophotometer
Serial Number         : 8002452
Software Version      : 2.0, Build 83 2.0.081
Method Name           : <Default Method>
Filename              :
Acquired              : May 07, 2012 9:54 AM Scan Mode             : Abs
Start Wavelength      : 200.0 nm
End Wavelength        : 800.0 nm
Wavelength Interval   : 1.0 nm
Scan Speed            : 1200 nm/min

#   Sample Name      Description
*   1   Sample 1-1       pxl
*   2   Sample 2-1       crm+
*   3   Sample 3-1       crm
```

Scan Graph

Wavelength Scan - Scanning     Figure 4     Print Date: May 07, 2012 10:34 AM

Wavelength Scan - Scanning

Print Date: May 07, 2012 10:47 AM

Non soluble Drugs
A. Camptothecin, B. Docetaxel, C. Paclitaxel, D. Bexarotene, E. Vitamin A F. Resveratrol
Water soluble Hybrids of same drugs
A. Camptothecin, B. Docetaxel, C. Paclitaxel, D. Bexarotene, E. Vitamin A F. Resveratrol

 Camptothecin
 Resveratrol
 Paclitaxel
 Vitamin A
 Bexarotene
Docetaxel
Figure 7

Soluble Hybrid Drugs

Figure 10
10A – untreated taxol resistant cell line
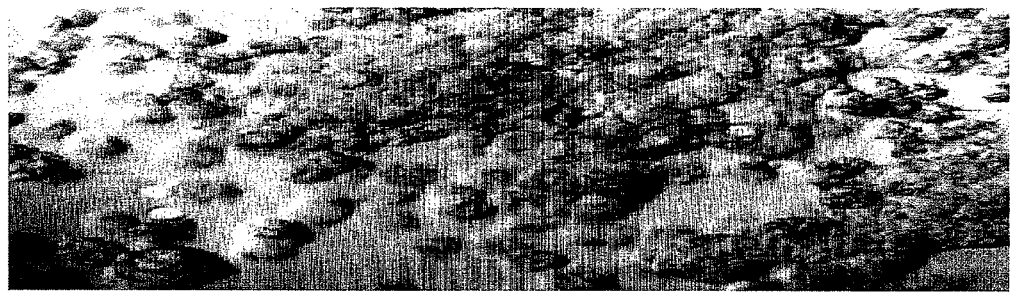
10 B – Cytopathic effects of hybrid Taxol on Taxol resistant cell lines

PHARMACEUTICAL COMPOSITIONS FOR THE DELIVERY OF SUBSTANTIALLY WATER-INSOLUBLE DRUGS

CROSS-REFERENCE TO RELATED APPLICATIONS

This application is a continuation-in-part of PCT Application No. PCT/US2013/035792, filed Apr. 9, 2013, which claims benefit under 35 U.S.C. §119(e) of U.S. Provisional Patent Application Ser. No. 61/647,727, filed on May 16, 2012, entitled PHARMACEUTICAL COMPOSITION, each of which is hereby fully incorporated by reference.

BACKGROUND OF THE INVENTION

1. Field of Invention

This invention relates to compositions and methods useful for the in vivo delivery of substantially water-insoluble drugs, like TAXOL®. The use of specific composition and preparation conditions enables the reproducible production of unusually water-soluble formulation, which can be sterile-filtered. The particulate system produced according to the invention can be converted into a re-dispersible dry powder comprising nanoparticles of drugs. This results in a unique delivery system, in which the pharmacologically active agent is readily bioavailable.

2. Description of Related Art

There are many valuable drugs which practically insoluble in water like the anticancer agent paclitaxel (TAXOL® for Injection Concentrate, Bristol Myers Squibb (BMS)) that reportedly has clinical activity or has been approved for use in a number of human cancers including cancers of the ovary, breast, lung, esophagus, head and neck region, bladder and lymphomas. It is currently approved for the treatment of certain stages of ovarian carcinoma, and non-small cell lung cancer; metastatic breast cancer; and for AIDS-related Kaposi's sarcoma.

A major limitation to the use of paclitaxel is its poor solubility and consequently the BMS formulation (TAXOL®) contains Cremophor® EL as a solubilizing vehicle. Each vial of TAXOL® contains 30 mg of paclitaxel dissolved in Cremophor/ethanol vehicle at a concentration of 6 mg/mL. Prior to intravenous administration, this formulation must be diluted 1:10 in saline to produce a final dosing solution containing 0.6 mg/mL of paclitaxel. Cremophor in this formulation has been linked to severe hypersensitivity reactions in animals (Lorenz et al., 1987, "Histamine Release in Dogs by Cremphor® EL® and its derivatives: Oxethylated oleic acid is the most effective constituent". Agents Actions 7:63-67, 1987) and humans (Weiss et al., 1990, "Hypersensitivity reactions from Taxol", J. Clin. Oncol. 8:1263-1268, 1990) and consequently requires premedication of patients with corticosteroids (dexamethasone) and antihistamines. The large dilution results in large volumes of infusion (typical dose 175 mg/m2) in up to one liter and infusion times ranging from three hours to 24 hours. Thus, there is a need for an alternative, less toxic formulation for water-insoluble drugs, such as paclitaxel, and other drugs of same nature.

ABRAXANE® (U.S. Pat. No. 6,537,579) is another paclitaxel formulation. It uses albumin to make small particles of the drug purportedly to make it more bioavailable, but has its own problems of manufacturing because of protein as a carrier more prone to contamination and antigenicity.

Docetaxel is an anti-cancer ("antineoplastic" or "cytotoxic") chemotherapy drug. This medication is classified as a "plant alkaloid," a "taxane" and an "antimicrotubule agent." The drug is prepared in polysorbate and 13% ethanol at the time of administration. The hybrid drug composition of the invention does not requires that all at all and is substantially soluble in water.

Bexarotene is indicated for the treatment of cutaneous manifestations of cutaneous T-cell lymphoma in people who are refractory to at least one prior systemic therapy (oral) and for the topical treatment of cutaneous lesions in patients with CTCL who have refractory or persistent disease after other therapies or who have not tolerated other therapies (topical). Bexarotene is a solid, white powder. It is poorly soluble in water; the solubility is estimated to be about 10-50 µM. It is soluble in DMSO at 65 mg/mL and in ethanol at 10 mg/mL with warming. The hybrid drug composition of the invention does not require that at all and is substantially soluble in water.

All-trans-retinoic acid can induce remission in acute promyelocytic leukemia. The molecule is not water-soluble. The hybrid drug composition of the invention is soluble in water.

The other drugs of invention are, for example, acetylsalicylic acid, resveratrol and diazepam.

The hybrids of the invention do not require any of the above material to make it more bioavailable, hence less toxic and more potent. In fact, the technology of the invention can make the drug more effective and less toxic.

The present invention includes compositions and methods useful for the in vivo delivery of substantially water-insoluble drugs, like taxol. The use of specific composition and preparation conditions enables the reproducible production of unusually water-soluble formulations, which can be sterile-filtered. The particulate system produced according to the invention can be converted into a re-dispersible dry powder comprising nanoparticles of drug. This results in a unique delivery system, in which at least part of the pharmacologically active agent is readily bioavailable.

Many drugs for parenteral use, especially those administered intravenously, cause undesirable side effects. These drugs are frequently water-insoluble, and are thus formulated with solubilizing agents, surfactants, solvents, and/or emulsifiers that may be irritating, allergenic, or toxic when administered to patients (see, e.g., Briggs et al., Anesthesis 37:1099 (1982), and Waugh et al., Am. J. Hosp. Pharmacists, 48:1520 (1991)). For example, the chemotherapeutic drug paclitaxel is active against a variety of carcinomas as mentioned above. Paclitaxel, however, has been shown to induce toxicities associated with administration, as well as significant acute and cumulative toxicity, such as myelosuppression, neutropenic fever, anaphylactic reaction, and peripheral neuropathy. Paclitaxel is very poorly water-soluble, and as a result, cannot be practically formulated with water for IV administration. Traditionally, paclitaxel is formulated for IV administration in a solution with polyoxyethylated castor oil (Cremophor) as the primary solvent and high concentrations of ethanol as cosolvent. Cremophor is associated with side effects that can be severe, including anaphylaxis and other hypersensitivity reactions that require pretreatment with corticosteroids, antihistamines, and H2 blockers (see, e.g., Gelderblom et al., Eur. J. of Cancer, 37:1590-1598, (2001)). Similarly, docetaxel is used in treatment of anthracycline-resistant breast cancer, but also has been shown to induce side effects of hypersensitivity and fluid retention that can be severe.

To circumvent problems associated with administration-related side effects of drug formulations, alternative formulations have been developed. For example, ABRAXANE® is a Cremophor-free, protein stabilized formulation of paclitaxel that was developed to resolve or minimize side effects caused by the Cremophor® EL/ethanol formulation. Similar protein-containing formulations have also been developed for other taxanes such as docetaxel and ortataxel, as well as other drugs.

Because protein serves as a good substrate for microbial growth, one major challenge encountered when using these protein-containing formulations is potential microbial contamination. For example, in order to minimize the risk of microbial contamination, the current intravenous formulation of Abraxane® is stored in lyophilized form, and should be injected immediately (e.g., within hours) after it is reconstituted in an aqueous medium. Bacterial growth can result from inadvertent contamination in a container containing a single dosage. Bacterial contamination is even more of a problem when multiple dosage withdrawals from the containers are needed.

Antibacterial agents such as EDTA, pentetate, or sulfites containing agents are generally known and used in pharmaceutical compositions. See, e.g., U.S. Pat. Nos. 5,714,520, 5,731,355, 5,731,356, 6,028,108, 6,100,302, 6,147,122, 6,177,477, 6,399,087, and 6,469,069, International Patent Application No. WO 99/39696, and U.S. Pat. Pub. No. 20050004002. Many of the antibacterial agents, however, are considerably toxic. For example, the addition of sulfites to drug formulations present potential adverse effects to the pediatric population and for those in the general population who are allergic to sulfur. See, e.g., Baker et al., Anesthesiology, 103(4):1-17 (2005); Mirejovsky, Am. J. Health Syst. Pharm., 58:1047 (2001). The toxicities of these antibacterial agents become a significant problem in formulating protein-containing pharmaceutical drug compositions, which frequently require more antimicrobial agents than non-protein containing formulations do in order to counter significant microbial growth therein.

Furthermore, many antimicrobial agents are known to interact with proteins and cause stability problems such as aggregation. See, e.g., Lam et al., Pharm. Res. 14:725-729 (1997). The effect of antimicrobial agents on protein stability raises a difficult issue in formulating protein-containing compositions of poorly water-soluble pharmaceutical agents, since proper configuration of proteins is generally required for stabilizing poorly water-soluble pharmaceutical agents in the composition.

There is therefore a need to develop a new strategy for poorly water-soluble pharmaceutical agents and which do not cause unacceptable toxicological effects upon administration.

There is need of developing a formulation which acts on the disease on multiple pathway of action while making the drug more bioavailable.

All references cited herein are incorporated herein by reference in their entireties.

BRIEF SUMMARY OF THE INVENTION

The invention provides a method of making a substantially water-solubilized hybrid drug composition comprising: a) providing a first active agent which is at least one substantially water-insoluble pharmacologically active agent; b) providing a second agent which is at least one complementary agent; and c) providing at least one polymer, d) dissolving the substantially water-insoluble pharmacologically active agent in an organic solvent; e) adding the first active agent in an organic solvent solution to a solution comprising the at least one complementary agent; f) adding the at least one polymer; g) homogenizing the mixture; h) sonicating the mixture to form nanoparticles; i) subjecting the mixture to evaporative drying, wherein the result of the process is a solubilized hybrid drug composition.

The invention provides a method further comprising the step of making a pharmaceutical composition by adding the solubilized hybrid drug composition to at least one pharmaceutically acceptable excipient. The invention further provides a method wherein the first active agent is the drug of main function and where the complementary drug which enhance the effects of primary drug. The invention further provides a method wherein the complementary agent has antioxidant properties. The invention further provides a method wherein the complementary agent is antimicrobial. The invention further provides a method wherein the complementary agent is anti-inflammatory.

The invention further provides a method wherein the complementary agent sensitizes the microenvironment of the disease. The invention further provides a method wherein the complementary agent is synergistic and potentiates the first active agent. The invention further provides a method wherein the complementary agent contributes to the solubility of the hybrid drug. The invention further provides a method wherein the first active agent is an anticancer molecule. The invention further provides a method wherein the first active agent is pain relief molecule. The invention further provides a method wherein the first active agent is a blood pressure or cholesterol related molecule. The invention further provides a method wherein the first active agent is an Alzheimer's drug.

The invention further provides a method wherein the polymer is soluble in alcohol as well as in water. The invention further provides a method further comprising the step of making a pharmaceutical dosage form by adding the solubilized hybrid drug composition to at least one pharmaceutically acceptable excipient. The invention further provides a method further comprising an additional drug compound, wherein the additional drug compound is selected from another group of molecule has a synergistic effect for the same disease, further wherein the additional drug is water-soluble or insoluble.

The invention further provides a method wherein the complementary agent is selected from the group consisting of selected from the group consisting of (a) curcumin; (b) a curcuminoid of formula (I)

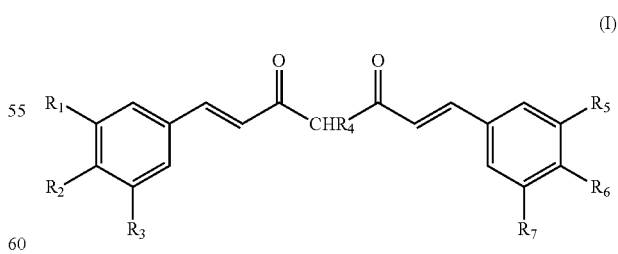

in which: (i) R1 is —H or —OCH3; R2 is —OH; R3 is —H; R4 is H; R5 is —H or OCH3; R6 is —OH, and R7 is —H, wherein only one of R1 and R5 is —OCH3; (ii) R1 is —H; R2 is —OH; R3 is —H or —OH; R4 is —H, R5 is —H; R6 is —OH; and R7 is —H or —OH; (iii) each of R1, R2, and R3 is —H, —OCH3, —OH, —ONa, acetyl, methyl, or ethyl; R4 is —H, —OH, ethyl, methyl, or acetyl; and each of R5, R6, and R7 is —H, —OCH3, —OH, —ONa, acetyl, methyl, or ethyl, wherein if R4 is —H or —OH, at least one of R2 and R6 is other than —H or —OH; (iv) R1 is —OH, R2 is —OH, R3 is —OH, R4 is —H or —OH, R5 is —OH, R6 is —OH; and R7 is —OH; (v) R1 is —OCH3; R2 is —OCH3; R3 is —OCH3; R4 is —H or —OH; R5 is —OCH3; R6 is —OCH3; and R7 is —OCH3; (vi) R1 is —H; R2 is —OCH3; R3 is —OCH3; R4 is —H or —OH; R5 is —H; R6 is —OCH3; and R7 is —OCH3; (vii) R1 is —H; R2 is —OH; R3 is —H; R4 is —H; R5 is —H or —OH; R6 is —OH; and R7 is —H; (viii) R1 is —H; R2 is —OCH3; R3 is —H; R4 is —H; R5 is —H or —OH; R6 is —OCH3; and R7 is —H; or (ix) R1 is —OH; R2 is —OCH3; R3 is —H or —OH; R4 is H or —OH; R5 is —OH; R6 is —OCH3; and R7 is —H or —OH; 19 (c) a curcuminoid of formula (II) in which the alternatives for R1 through R7 are the same as those recited in paragraph (b);

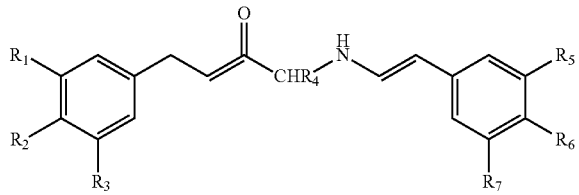

(II)

(d) a curcuminoid of formula (III) in which the alternatives for R1 through R7 are the same as those recited in paragraph (b);

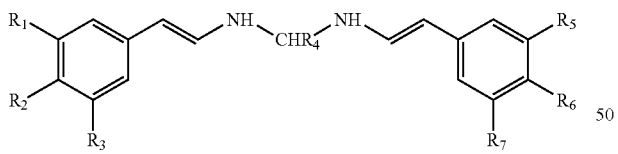

(III)

(e) the compound of formula (IV)

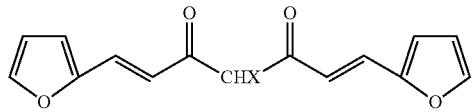

(IV)

in which X is —H, the compound being designated furfural curcuminoid;

(f) an analogue of furfural curcuminoid in which X is —OH, ethyl, methyl, or acetyl;

(g) the compound of formula (V)

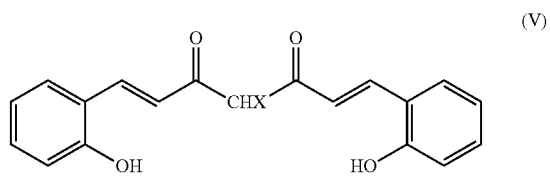

(V)

in which X is —H, the compound being designated salicyl curcuminoid; (h) an analogue of salicyl curcuminoid in which X is —OH, ethyl, methyl, or acetyl;

(i) the compound of formula (VI)

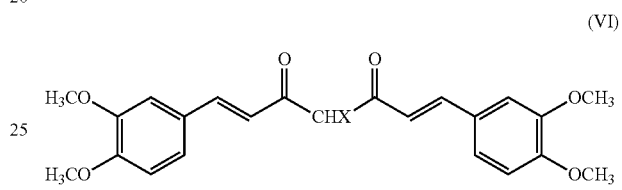

(VI)

in which X is —H, the compound being designated veratryl curcuminoid;

(j) an analogue of veratryl curcuminoid in which X is —OH, ethyl, methyl, or acetyl;

(k) the compound of formula (VII) in which X is —H, the compound being designated p-anisyl curcuminoid;

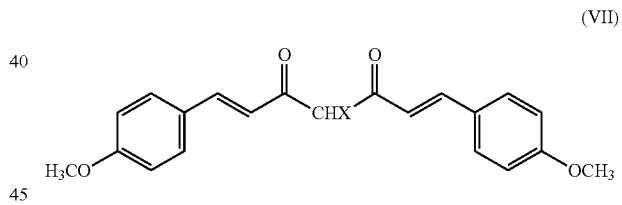

(VII)

(l) an analogue of p-anisyl curcuminoid in which X is —OH, ethyl, methyl, or acetyl;

(m) the compound of formula (VIII)

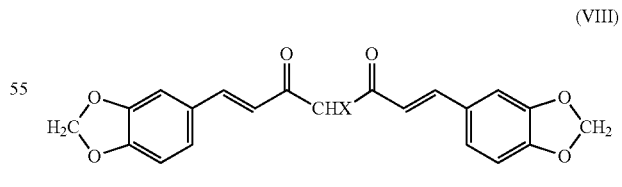

(VIII)

in which X is —H, the compound being designated piperonal curcuminoid;

(n) an analogue of piperonal curcuminoid in which X is —OH, ethyl, methyl, or acetyl;

(o) a tetrahydrocurcuminoid of formula (IX) in which the alternatives for R1 through R7 are the same as those recited in paragraph (b);

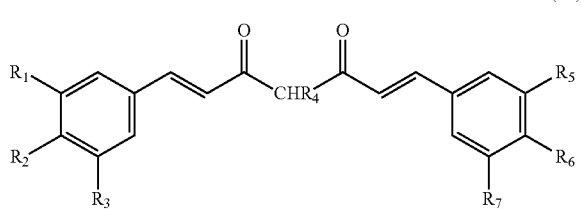

(p) a curcuminoid of formula (X) in which the alternatives for R1 through R7 are the same as those recited in paragraph (b);

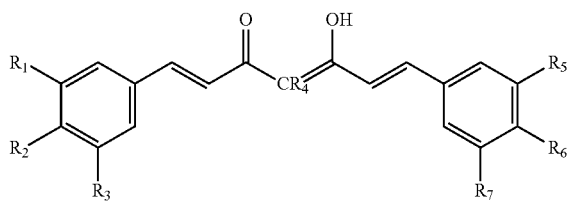

(q) a curcuminoid of formula (XI)

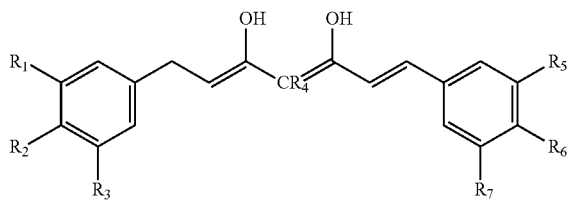

in which the alternatives for R1 through R7 are the same as those recited in paragraph (b);

(r) a reduced curcuminoid of formula (XII) in which the alternatives for R1 through R7 are the same as those recited in paragraph (b);

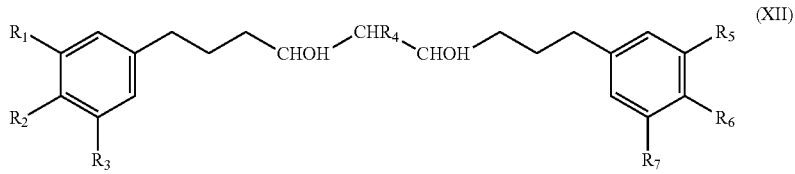

(s) derivatives of the compounds recited in (b) through (r) in which any of the methoxy groups are replaced with lower alkoxy groups selected from the group consisting of ethoxy, n-propoxy, and isopropoxy; (t) derivatives of the compounds recited in (b) through (r) in which any of the hydroxy groups of the phenolic moieties are substituted with an acyl group selected from the group consisting of acetyl, propionyl, butyryl, and isobutyryl; (u) analogues of the compounds recited in (b), (c), and (e) through (p) in which one or both of the carbonyl (CO) groups are replaced by amino (NH) groups in analogy with formulas II and III; and (v) analogues of the compounds recited in (b), (c), and (e) through (p) in which one or both of the oxygens of the carbonyl groups are replaced by sulfur to form thiocarbonyl groups; and combinations thereof.

The invention further provides a method wherein the first active agent is selected from the group consisting of paclitaxel, albumin-bound paclitaxel, docetaxel, bexarotene, all-5 trans-retinoic acid, and combinations thereof. The invention further provides a method wherein the polymer is selected from the group consisting of methylcellulose, hydroxyethyl cellulose, hydroxypropyl cellulose, hydroxypropyl methylcellulose, hydroxypropyl ethylcellulose, sodium carboxymethylcellulose, polyvinyl alcohol, polyvinylpyrrolidone, polyethylene glycol, poly(methyl methacrylate), polycarbophil, gelatin, alginate, 10 poly(acrylic acid), polyethylene oxide, chitosan, derivatives thereof, and mixtures thereof. The invention further provides a method wherein the polymer is selected from the group consisting of water-soluble, alcohol soluble, organic soluble, and combinations thereof. The invention further provides a method wherein the polymer carrier is one or more selected from the group consisting of hydroxypropylmethylcellulose (HPMC), polyethyleneglycol 15 (PEG), polyvinylpyrrolidone (PVP), cellulose polymer, and a combination thereof.

The invention further provides a method wherein the polymer carrier is hydroxypropylmethylcellulose. The invention further provides a method wherein the polymer is 1 to 5 times of the concentration of the second active agent. The invention further provides a method wherein the at least organic solvent is ethanol. The invention further provides a method wherein the weight ratio of the first active agent and the water-soluble polymer carrier is 1:1 to 1:15. The invention further provides a method wherein the organic solvent is selected from the group consisting of C1-C4 linear or branched alcohol, and a combination thereof. The invention further provides a method wherein the weight ratio of the organic solvent and water is 0.5:1 to 5:1.

The invention provides a composition comprising: i) a first active agent which is at least one substantially water-insoluble pharmacologically active agent; ii) a second agent which is at least one complementary agent, which is water-insoluble or water-soluble, and iii) a polymer, wherein the first active agent is dissolved in an organic solvent, and the solution is added to a solution comprising the at least one complementary agent, the polymer is added, the mixture is homogenized, then sonicated to form nanoparticles, and subject to evaporative drying.

The invention further provides a composition wherein the complementary agent is selected from the group consisting of (a) curcumin; (b) a curcuminoid of formula (I)

(I)

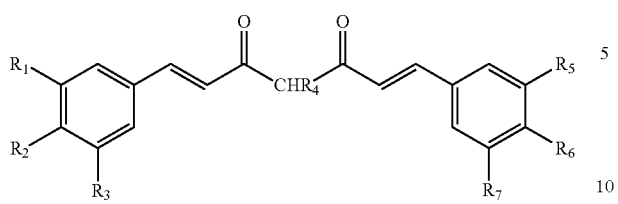

in which: (i) R1 is —H or —OCH3; R2 is —OH; R3 is —H; R4 is H; R5 is —H or OCH3; R6 is —OH, and R7 is —H, wherein only one of R1 and R5 is —OCH3; (ii) R1 is —H; R2 is —OH; R3 is —H or —OH; R4 is —H, R5 is —H; R6 is —OH; and R7 is —H or —OH; (iii) each of R1, R2, and R3 is —H, —OCH3, —OH, —ONa, acetyl, methyl, or ethyl; R4 is —H, —OH, ethyl, methyl, or acetyl; and each of R5, R6, and R7 is —H, —OCH3, —OH, —ONa, acetyl, methyl, or ethyl, wherein if R4 is —H or —OH, at least one of R2 and R6 is other than —H or —OH; (iv) R1 is —OH, R2 is —OH, R3 is —OH, R4 is —H or —OH, R5 is —OH, R6 is —OH; and R7 is —OH; (v) R1 is —OCH3; R2 is —OCH3; R3 is —OCH3; R4 is —H or —OH; R5 is —OCH3; R6 is —OCH3; and R7 is —OCH3; (vi) R1 is —H; R2 is —OCH3; R3 is —OCH3; R4 is —H or —OH; R5 is —H; R6 is —OCH3; and R7 is —OCH3; (vii) R1 is —H; R2 is —OH; R3 is —H; R4 is —H; R5 is —H or —OH; R6 is —OH; and R7 is —H; (viii) R1 is —H; R2 is —OCH3; R3 is —H; R4 is —H; R5 is —H or —OH; R6 is —OCH3; and R7 is —H; or (ix) R1 is —OH; R2 is —OCH3; R3 is —H or —OH; R4 is H or —OH; R5 is —OH; R6 is —OCH3; and R7 is —H or —OH; 19 (c) a curcuminoid of formula (II) in which the alternatives for R1 through R7 are the same as those recited in paragraph (b);

(II)

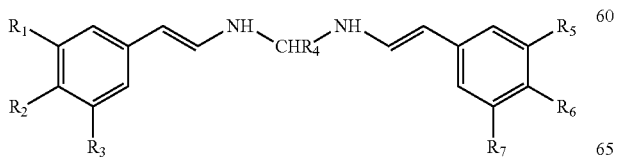

(d) a curcuminoid of formula (III) in which the alternatives for R1 through R7 are the same as those recited in paragraph (b);

(III)

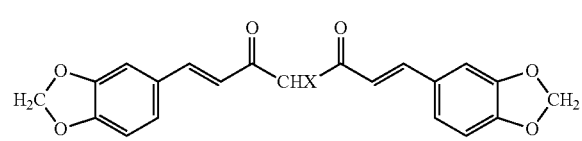

(e) the compound of formula (IV)

(IV)

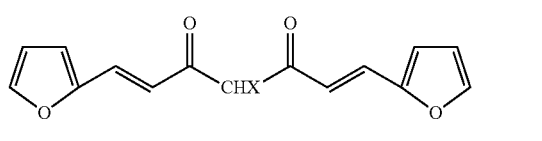

in which X is —H, the compound being designated furfural curcuminoid;
(f) an analogue of furfural curcuminoid in which X is —OH, ethyl, methyl, or acetyl;
(g) the compound of formula (V)

(V)

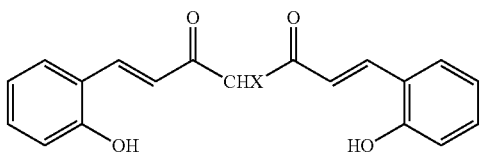

in which X is —H, the compound being designated salicyl curcuminoid; (h) an analogue of salicyl curcuminoid in which X is —OH, ethyl, methyl, or acetyl;
(i) the compound of formula (VI)

(VI)

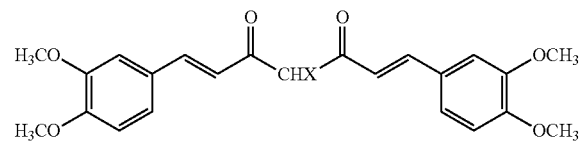

in which X is —H, the compound being designated veratryl curcuminoid;
(j) an analogue of veratryl curcuminoid in which X is —OH, ethyl, methyl, or acetyl;
(k) the compound of formula (VII) in which X is —H, the compound being designated p-anisyl curcuminoid;

(VII)

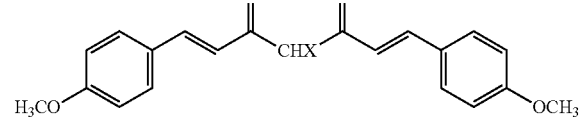

(l) an analogue of p-anisyl curcuminoid in which X is —OH, ethyl, methyl, or acetyl;
(m) the compound of formula (VIII)

(VIII)

in which X is —H, the compound being designated piperonal curcuminoid;

(n) an analogue of piperonal curcuminoid in which X is —OH, ethyl, methyl, or acetyl;

(o) a tetrahydrocurcuminoid of formula (IX) in which the alternatives for R1 through R7 are the same as those recited in paragraph (b);

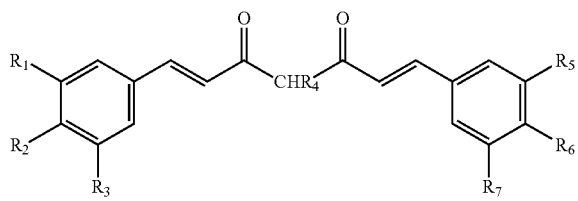

(p) a curcuminoid of formula (X) in which the alternatives for R1 through R7 are the same as those recited in paragraph (b);

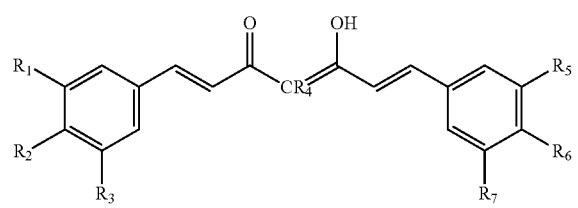

(q) a curcuminoid of formula (XI)

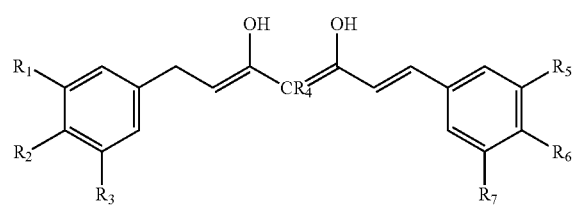

in which the alternatives for R1 through R7 are the same as those recited in paragraph (b);

(r) a reduced curcuminoid of formula (XII) in which the alternatives for R1 through R7 are the same as those recited in paragraph (b);

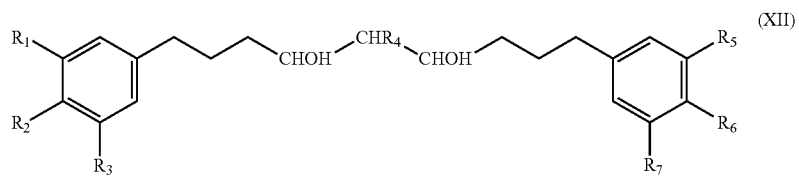

(s) derivatives of the compounds recited in (b) through (r) in which any of the methoxy groups are replaced with lower alkoxy groups selected from the group consisting of ethoxy, n-propoxy, and isopropoxy; (t) derivatives of the compounds recited in (b) through (r) in which any of the hydroxy groups of the phenolic moieties are substituted with an acyl group selected from the group consisting of acetyl, propionyl, butyryl, and isobutyryl; (u) analogues of the compounds recited in (b), (c), and (e) through (p) in which one or both of the carbonyl (CO) groups are replaced by amino (NH) groups in analogy with formulas II and III; and (v) analogues of the compounds recited in (b), (c), and (e) through (p) in which one or both of the oxygens of the carbonyl groups are replaced by sulfur to form thiocarbonyl groups; and combinations thereof.

The invention further provides a composition wherein the first active agent is selected from the group consisting of paclitaxel, docetaxel, bexarotene, All-trans-retinoic acid, acetylsalicylic acid, resveratrol, diazepam and combinations thereof. The invention further provides a composition comprising a first active agent, a complimentary agent, and a polymer for bridging. The invention further provides a composition wherein the first active agent is the drug of main function and where the complementary agent enhances the effects of the first active agent. The invention further provides a composition wherein the complementary agent has antioxidant properties.

The invention further provides a composition wherein the complementary agent is antimicrobial. The invention further provides a composition wherein the complementary agent is anti-inflammatory. The invention further provides a composition wherein the complementary agent sensitizes the microenvironment of the disease. The invention further provides a composition wherein the complementary agent is synergistic and potentiates the first active agent. The invention further provides a composition wherein the complementary agent contributes to the solubility of the hybrid drug. The invention further provides a composition wherein the first active agent is an anticancer molecule. The invention further provides a composition wherein the first active agent is a pain relief molecule.

The invention further provides a composition wherein the first active agent is a blood pressure or cholesterol related molecule. The invention further provides a composition wherein the first active agent is an alzheimer's drug. The invention further provides a composition wherein the polymer is soluble in alcohol as well as in water. The invention further provides a composition wherein the polymer is selected from the group consisting of polyvinylpyrrolidone, polyethylene glycol, derivatives thereof, and mixtures thereof. The invention further provides a composition wherein the polymer carrier is one or more selected from the group consisting of hydroxypropylmethylcellulose (HPMC), polyethyleneglycol (PEG), polyvinylpyrrolidone (PVP), cellulose polymer, and a combination thereof. The invention further provides a composition wherein the polymer carrier is PVP. The invention further provides a composition wherein the weight ratio of the poorly soluble drug and the polymer carrier is 1:1 to 1:15. The invention provides a pharmaceutical composition comprising the composition of the invention and at least one pharmaceutically acceptable excipient. The invention provides a pharmaceutical dosage form comprising the composition of the invention and at least one pharmaceutically acceptable excipient.

The invention provides a method of making a substantially water-solubilized hybrid drug composition of the invention wherein the first active agent is selected from the group consisting of Acemetacin, 5-aminosalicylic acid, Aspirin, Artemisinin, Aripiprazole, Ariprepitant, Azacitidine, Azathioprine, Azithromycin, Azithromycin dihydrate, Bacitracin, Bexarotene Free Acid, Budesonide, Budesonide 98%, Camphor, Camptothecin, Carmustine, Capecitabine, Carbamazepine, Carbenicillin disodium salt, Celecoxib, Cisplatin, Clopidogrel Sulfate, Colchicine, Combrestastatin A4, Curcumin, Cyclosporin A, Daunorubicin hydrochloride, Dexamethasone, Dihydroergotamine Mesylate, Digooxin, Docetaxel, Epothilone A, Erlotinib Monohydrochloride, β-Estradiol, Fexofenadine HCl, Griseofulvin, Ibuprofen, Itraconazole, Ivermectin, Lenalidomide, Leucovorin Calcium, Loperamide HCL, Loratadine, Magestrol Acetate, Methotrexate, Mevastatin, Naproxen, Nefedipine, Nystatin mycostatin, Nimodipine, Ofloxacin, Olanzapine, Paclitaxel, Paliperidone, Pomalidomide, Pravastatin Sodium, Prednisone, Quinine, Rapamycin, Resveratrol, Retinonic acid, Rifampin, Rlaxifene hcl, Statine, Sidenafil Citrate, Sildenafil Citrate >99%, sorafenib, Sulfasalazine, Tadalafil, Telaprevir, Temozolomide, Torisamide, Thalidomide, Valsartan, Vardenafil hydrocholoride trihydrate, Variconazole, Zidovudine, and Ziprasidone hydrocholoride, and combinations thereof.

The invention provides a method of making a substantially water-solubilized hybrid drug composition wherein the first active agent is selected from the group consisting of, for example, Acemetacin, Acetatamiprid, Alfa-cypermethrin, 5-aminosalicylic acid, Amiodarone, Amiodipine, Aspirin, Aprepitant, Artemisinin, Aripiprazole, 99%, Astemizole, Azacitidine (Vidaza), Azadirectin, Azathioprine, Azelastine, Azithromycin-dihydrate, Bacitracin, Beta Carotenene, Beta-sitosterol, Bexarotene, Free Acid (4), Budesonide, 98%, Busulphan, Camphor, Camptothecin, Cannabinoids, Carmustine, Carvedilol, Capecitabine, Carbamazepine, Carbenicillin disodium, Cephalexin, Cefotaxime, Celecoxib, Chlorfenapyr, Chlorantraniliprole, Cilostazol, Cisplatin, Clarithromycin, Clopidogrel Sulfate, Colchicine, CoQ10, Combrestastatin A4, Curcumin (2 cc.) for injection, Cyclophosphomide, Cyclosporin A, Cymoxanil, Daunorubicin hydrochloride, Dexamethasone, Diaminodiphenyl sulfone, 6-(2,3-Dichlorophenyl)-1,2,4-triazine-3,5-diamine (Lamotrigine), Diclofenac, Dihydroergotamine Mesylate, Digooxin, Diindolylmethane,3,3, Docetaxel, Doxorubicin, Domperidone, Epothilone A, Escitalopram, Erlotinib Monohydrochloride, β-Estradiol, Etodolac, Etoposide, Famotidine, Fenazaquin, Fexofenadine hcl, Finasteride, Finofibrate, Fluconazole (candida), Fluticasone Propionate, Genistein, Griseofulvin, Ibuprofen, Indomethacin, Indoxacarb, Irbessartan (no EthOH), Itraconazole, Ivermectin, Lavamisloe, Lenalidomide, Leucovorin Calcium, Lidocaine, Loperamide HCL, Loratadine, Kaempferol, Ketoprofen, Magestrol Acetate, Mechlorethamine, Melphalan, Methotrexate, Mevastatin, Minimum 95% HPLC, Naproxen, Nebumelon, Nefedipine, Norfloxacin, Nystatin mycostatin, Nimodipine, Ofloxacin, Olanzapine, Opioid, Paclitaxel from Taxus Brevifolia, Paliperidone, Paracetamol, PCI-32765, Piroxicam, Pomalidomide, Pravastatin Sodium, Prethrin, Prednisone, Propanil pestanal, Pyrimethamine, Quinine, Rapamycin, Resveratrol, Retinonic acid 97%, Rifampin, Reloxifene hcl, Rosiglitazone, Saquinavir, Statine, Sidenafil Citrate >99%, Sorafenib, Sulcotrione, Sulfasalazine, Tadalafil (Cialis), Tebuconazole, Telaprevir, Temozolomide, Terbinafine, Tamoxifen, Thalidomide, Thiacloprid, Thiram, Torisamide, Triamcinolone, Tribenuron methyl, Valsartan 99%, Vardenafil hydrocholoride trihydrate, Variconazole, Vitamin D3, Zidovudine, Ziprasidone, Zoledronic acid, and combinations thereof.

The invention provides a composition of the invention wherein the first active agent is selected from the group consisting of, for example, Acemetacin, Acetatamiprid, Alfa-cypermethrin, 5-aminosalicylic acid, Amiodarone, Amiodipine, Aspirin, Aprepitant, Artemisinin, Aripiprazole, 99%, Astemizole, Azacitidine (Vidaza), Azadirectin, Azathioprine, Azelastine, Azithromycin-dihydrate, Bacitracin, Beta Carotenene, Beta-sitosterol, Bexarotene, Free Acid (4), Budesonide, 98%, Busulphan, Camphor, Camptothecin, Cannabinoids, Carmustine, Carvedilol, Capecitabine, Carbamazepine, Carbenicillin disodium, Cephalexin, Cefotaxime, Celecoxib, Chlorfenapyr, Chlorantraniliprole, Cilostazol, Cisplatin, Clarithromycin, Clopidogrel Sulfate, Colchicine, CoQ10, Combrestastatin A4, Curcumin (2 cc.) for injection, Cyclophosphomide, Cyclosporin A, Cymoxanil, Daunorubicin hydrochloride, Dexamethasone, Diaminodiphenyl sulfone, 6-(2,3-Dichlorophenyl)-1,2,4-triazine-3,5-diamine (Lamotrigine), Diclofenac, Dihydroergotamine Mesylate, Digooxin, Diindolylmethane,3,3, Docetaxel, Doxorubicin, Domperidone, Epothilone A, Escitalopram, Erlotinib Monohydrochloride, β-Estradiol, Etodolac, Etoposide, Famotidine, Fenazaquin, Fexofenadine hcl, Finasteride, Finofibrate, Fluconazole (candida), Fluticasone Propionate, Genistein, Griseofulvin, Ibuprofen, Indomethacin, Indoxacarb, Irbessartan (no EthOH), Itraconazole, Ivermectin, Lavamisloe, Lenalidomide, Leucovorin Calcium, Lidocaine, Loperamide HCL, Loratadine, Kaempferol, Ketoprofen, Magestrol Acetate, Mechlorethamine, Melphalan, Methotrexate, Mevastatin, Minimum 95% HPLC, Naproxen, Nebumelon, Nefedipine, Norfloxacin, Nystatin mycostatin, Nimodipine, Ofloxacin, Olanzapine, Opioid, Paclitaxel from Taxus Brevifolia, Paliperidone, Paracetamol, PCI-32765, Piroxicam, Pomalidomide, Pravastatin Sodium, Prethrin, Prednisone, Propanil pestanal, Pyrimethamine, Quinine, Rapamycin, Resveratrol, Retinonic acid 97%, Rifampin, Reloxifene hcl, Rosiglitazone, Saquinavir, Statine, Sidenafil Citrate >99%, Sorafenib, Sulcotrione, Sulfasalazine, Tadalafil (Cialis), Tebuconazole, Telaprevir, Temozolomide, Terbinafine, Tamoxifen, Thalidomide, Thiacloprid, Thiram, Torisamide, Triamcinolone, Tribenuron methyl, Valsartan 99%, Vardenafil hydrocholoride trihydrate, Variconazole, Vitamin D3, Zidovudine, Ziprasidone, Zoledronic acid, and combinations thereof, and combinations thereof.

The invention provides a topical pharmaceutical formulation for use in treatment of a subject, comprising a composition of the invention, and at least one pharmaceutically acceptable excipient. The invention further provides a topical formulation of the invention wherein said formulation is in a form selected from the group consisting of: cream, lotion, gel, oil, ointment, suppository, spray, foam, liniment, aerosol, buccal and sublingual tablet or a transdermal device for absorption through the skin or mucous membranes. The invention further provides a topical formulation of the invention wherein said pharmaceutical formulation is a transdermal patch. The invention further provides a topical formulation of the invention wherein said pharmaceutical formulation is a buccal formulation.

The invention provides a method of the invention wherein the first active agent is selected from the group consisting of, for example, Acemetacin, Acetatamiprid, Alfa-cypermethrin, 5-aminosalicylic acid, Amiodarone, Amiodipine, Aspirin, Aprepitant, Artemisinin, Aripiprazole, 99%, Astemizole, Azacitidine (Vidaza), Azadirectin, Azathioprine, Azelastine, Azithromycin-dihydrate, Bacitracin, Beta Carotenene, Beta-sitosterol, Bexarotene, Free Acid (4), Budesonide, 98%, Busulphan, Camphor, Camptothecin, Cannabinoids, Carmustine, Carvedilol, Capecitabine, Carbamazepine, Carbenicillin disodium, Cephalexin, Cefotaxime, Celecoxib, Chlorfenapyr, Chlorantraniliprole, Cilostazol, Cisplatin, Clarithromycin, Clopidogrel Sulfate, Colchicine, CoQ10, Combrestastatin A4, Curcumin (2 cc.) for injection, Cyclophosphomide, Cyclosporin A, Cymoxanil, Daunorubicin hydrochloride, Dexamethasone, Diaminodiphenyl sulfone, 6-(2,3-Dichlorophenyl)-1,2,4-triazine-3, 5-diamine (Lamotrigine), Diclofenac, Dihydroergotamine Mesylate, Digooxin, Diindolylmethane,3,3, Docetaxel, Doxorubicin, Domperidone, Epothilone A, Escitalopram, Erlotinib Monohydrochloride, β-Estradiol, Etodolac, Etoposide, Famotidine, Fenazaquin, Fexofenadine hcl, Finasteride, Finofibrate, Fluconazole (*candida*), Fluticasone Propionate, Genistein, Griseofulvin, Ibuprofen, Indomethacin, Indoxacarb, Irbessartan (no EthOH), Itraconazole, Ivermectin, Lavamisloe, Lenalidomide, Leucovorin Calcium, Lidocaine, Loperamide HCL, Loratadine, Kaempferol, Ketoprofen, Magestrol Acetate, Mechlorethamine, Melphalan, Methotrexate, Mevastatin, Minimum 95% HPLC, Naproxen, Nebumelon, Nefedipine, Norfloxacin, Nystatin mycostatin, Nimodipine, Ofloxacin, Olanzapine, Opioid, Paclitaxel from *Taxus Brevifolia*, Paliperidone, Paracetamol, PCI-32765, Piroxicam, Pomalidomide, Pravastatin Sodium, Prethrin, Prednisone, Propanil pestanal, Pyrimethamine, Quinine, Rapamycin, Resveratrol, Retinonic acid 97%, Rifampin, Reloxifene HCl, Rosiglitazone, Saquinavir, Statine, Sidenafil Citrate >99%, Sorafenib, Sulcotrione, Sulfasalazine, Tadalafil (Cialis), Tebuconazole, Telaprevir, Temozolomide, Terbinafine, Tamoxifen, Thalidomide, Thiacloprid, Thiram, Torisamide, Triamcinolone, Tribenuron methyl, Valsartan 99%, Vardenafil hydrocholoride trihydrate, Variconazole, Vitamin D3, Zidovudine, Ziprasidone, Zoledronic acid, and combinations thereof.

The invention further provides a method for treating a patient in need of such treatment comprising administration of a pharmaceutical composition of the invention.

BRIEF DESCRIPTION OF THE DRAWING

The invention will be described in conjunction with the following drawing in which like reference numerals designate like elements and wherein:

FIG. 1 is a comparative study conducted to evaluate the activity of paclitaxel and water-soluble paclitaxel. The Taxol hybrid is more potent as compared to Taxol in vitro using cancer cell lines. The results indicated a 50 fold more in vitro activity.

FIG. 7 shows the insolubility of the water-insoluble drugs. The crystals of various drugs in native form and which are not water soluble.

FIG. 10 shows the cytopathic effects of hybrid Taxol on a Taxol resistant cell line. FIG. 10A. A taxol resistant cell line without treatment (in vitro) showing aggressive growth. FIG. 10B. The same cell line treated with the hybrid taxol, showing cytopathic effects. The hybrid inhibits the growth as well as kills the cells.

DETAILED DESCRIPTION OF THE INVENTION

Figure 2:
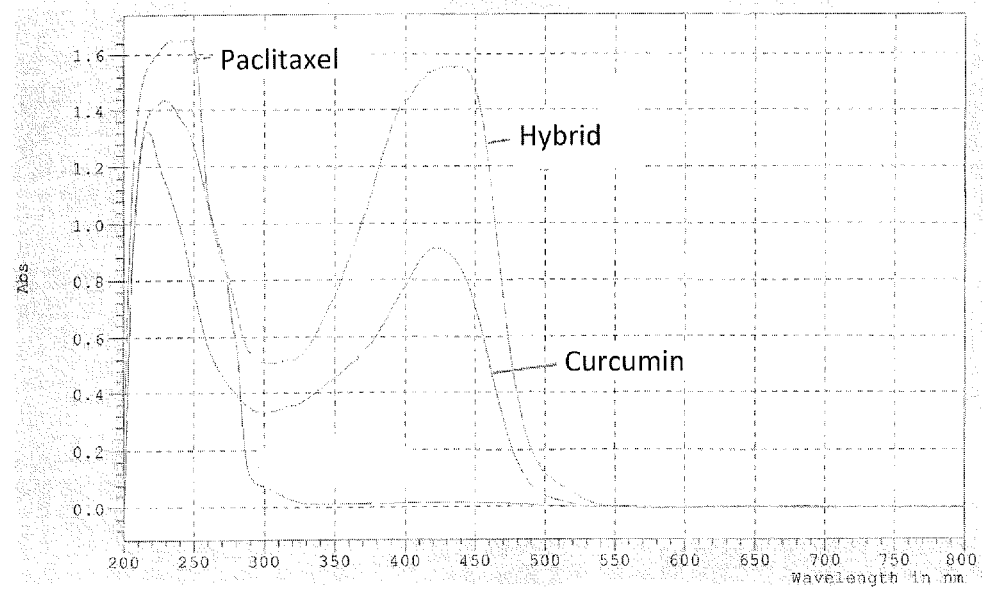
FIG. 2 shows Paclitaxel hybrid spectrophotometric analysis and observed shift in absorption peak. The spectrophotometric graphic of the absorbance value of paclitaxel, curcumin, and the paclitaxel-curcumin hybrid are indicated. Absorption spectra of samples were measured from 200 to 800 nm in a UV-Vis spectrometer (DU 800; Beckman Coulter, Indianapolis, Ind.).
Figure 3:
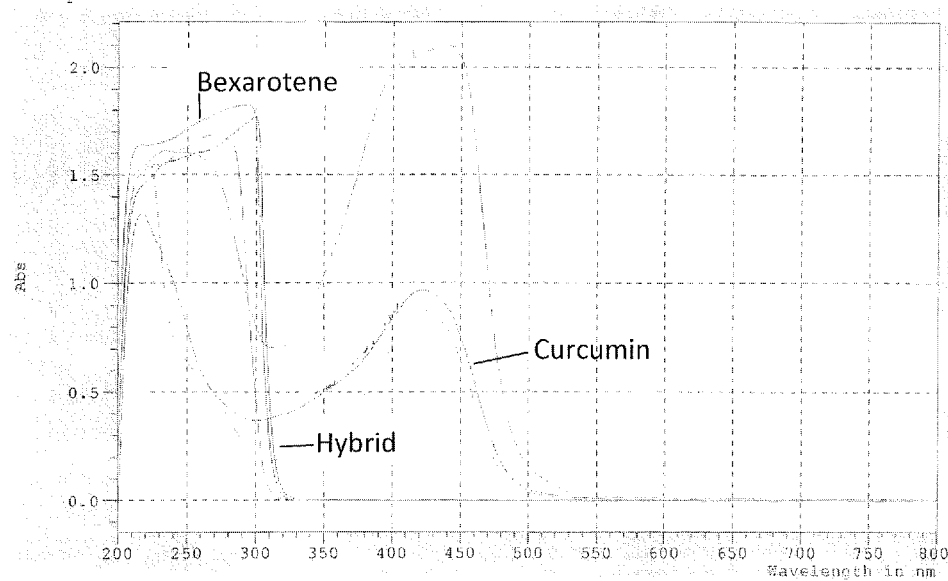
FIG. 3 shows bexarotene hybrid spectrophotometric analysis and observed shift in absorption peak. The spectrophotometric graphic of the absorbance value of bexarotene, curcumin, and the bexarotene-curcumin hybrid are indicated.
Figure 4:
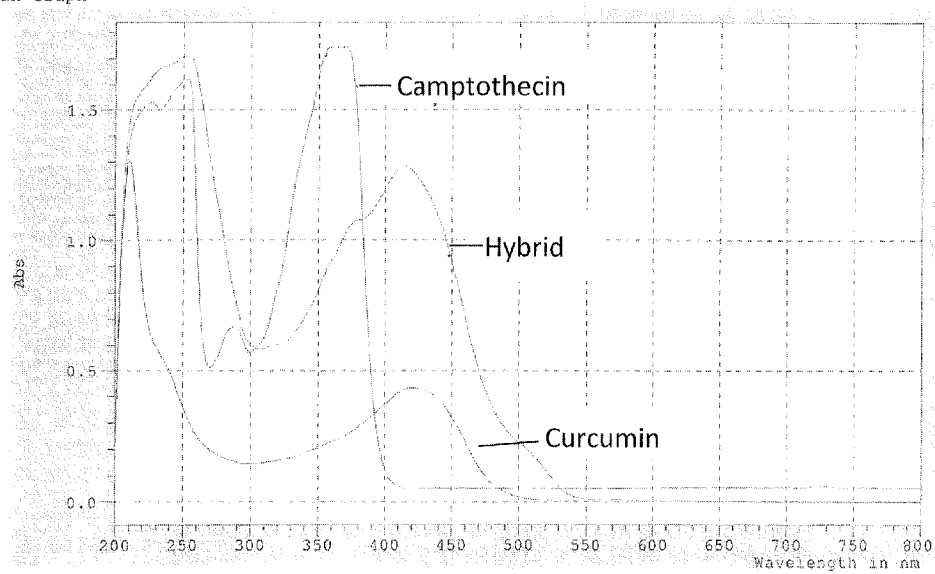
FIG. 4 shows camptothecin hybrid spectrophotometric analysis and observed shift in absorption peak. The spectrophotometric graphic of the absorbance value of camptothecin, curcumin, and the camptothecin-curcumin hybrid are indicated.
Figure 5:
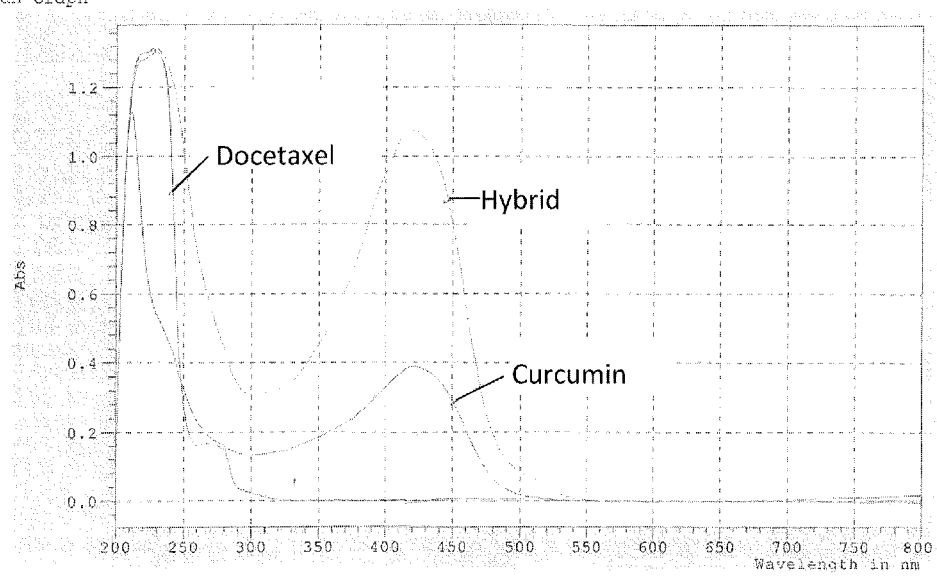
FIG. 5 shows docetaxel hybrid spectrophotometric analysis and observed shift in absorption peak. The spectrophotometric graphic of the absorbance value of docetaxel, curcumin, and the docetaxel-curcumin hybrid are indicated.
Figure 6:
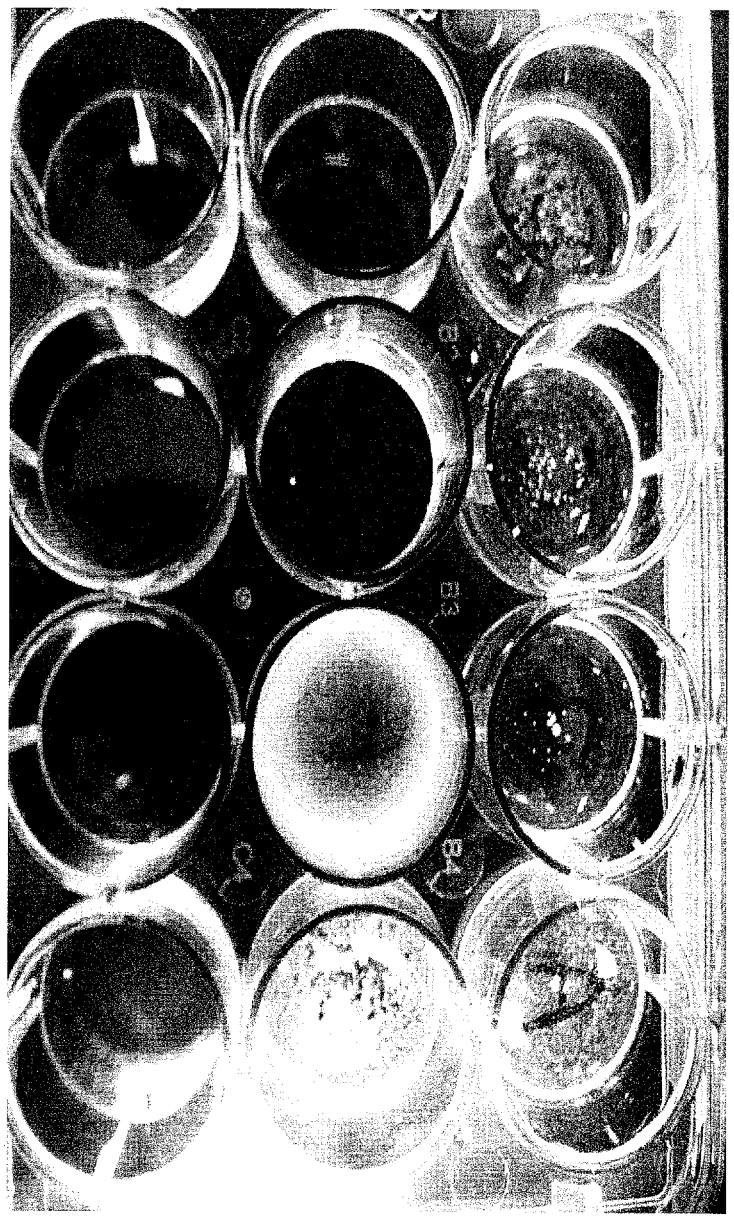
FIG. 6 shows the solubility of the water-insoluble drugs, and the improved solubility of the hybrid drugs. Non soluble drugs become soluble in the hybrid drugs of the invention.
Figure 8:
FIG. 8 shows the improved solubility of the hybrid drugs. The hybrids are water soluble and the crystals of the original drugs are no longer visible under the microscope, that otherwise are visible in original drugs.
Figure 9:
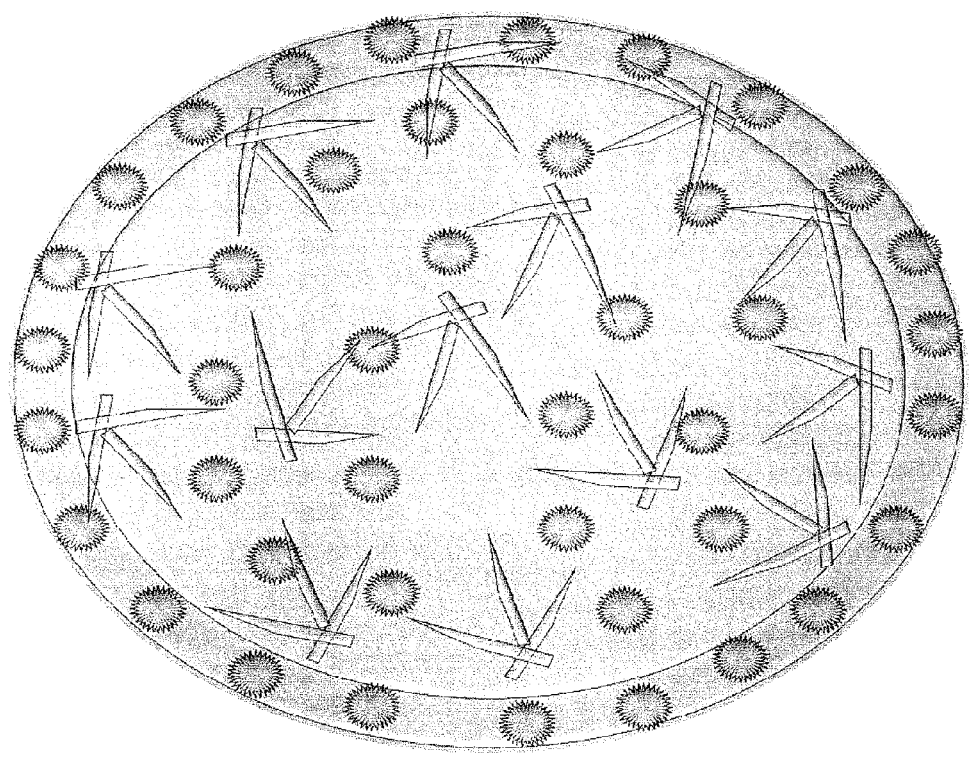
FIG. 9 is a diagrammatic representation of a hybrid drug, showing an exemplary embodiment wherein the polymer acts as a bridge between the water-insoluble active agent and the complementary agent.
Figure 11:
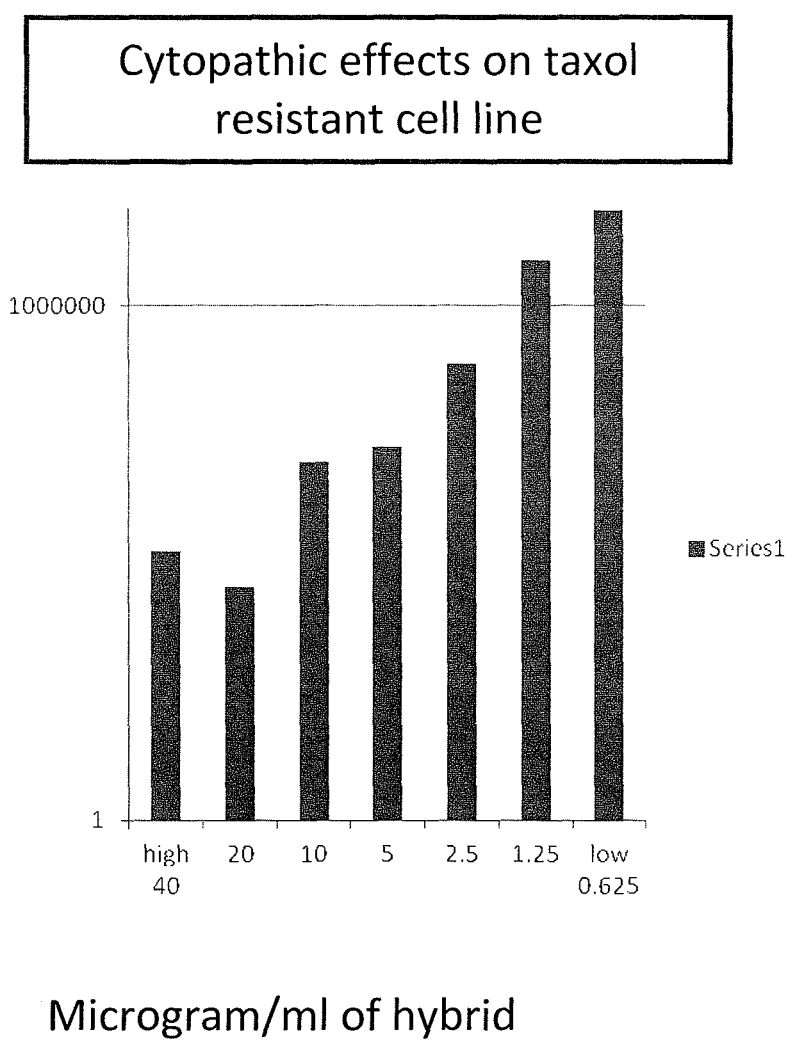
FIG. 11 shows that cytopathic effects are observed even at a very low concentration of Taxol (5 microgram/ml) using Taxol resistant cell line.
Figure 12:
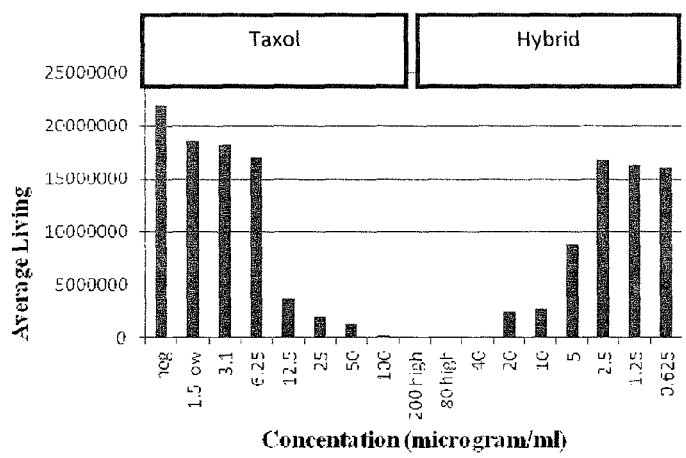
FIG. 12 shows comparative cytopathic effects observed on cancer cell line. The hybrid Taxol is much more potent than Taxol.

The inventors have designed compositions and methods useful for the in vivo delivery of substantially water-insoluble drugs, like taxol. The use of specific composition and preparation conditions enables the reproducible production of unusually water-soluble formulation, which can be sterile-filtered. The particulate system produced according to the invention can be converted into a re-dispersible dry powder comprising nanoparticles of drug and drugs. This results in a unique delivery system, in which part of the pharmacologically active agent is readily bioavailable.

One example of a water-insoluble drug compound is paclitaxel, which is a valuable therapeutic drug with the significance disadvantage which is its low solubility. The inventors have resolved the problem, and made paclitaxel not only in water-soluble form but also potentiating the effects. The invention has the surprising advantage of making the compounds of the invention more potent and less toxic. The inventors have achieved the following surprising in this invention: (a) drug is less toxic (b) drug is more potent (c) drug is water-soluble and hence more bioavailable and (d) hybrid drug is synergistic and potentiating the effects of each other.

Currently, to make water-insoluble drugs suitable for in vivo use these compounds are treated with oil which can be toxic, alcohol which can be toxic, and/or albumin which can be immunogenic. These molecules add up in toxicity of the drug. The inventors have resolved the problem and made formulations which do not require any of these carriers. Because of its water-soluble nature, the formulation is more potent and less toxic. These factors may contribute to its less expensive manufacturing cost as well as saving cost at the site of administration.

In accordance with the present invention, there are provided compositions and methods useful for the in vivo delivery of substantially water-insoluble pharmacologically active agents (such as, for example, the anticancer drug paclitaxel, camptothecin, bexarotene, docetaxel, all trans retinoic acid, etc.) in which the pharmacologically active agent is delivered in the form of hybrid drug (which becomes water-soluble). In particular, hybridizing agent and pharmacologically active agent in a biocompatible dispersing medium are subjected to hybridization. The procedure yields particles with a diameter in nanosize. The particulate system produced according to the invention can be converted into a redispersible dry powder comprising nanoparticles of water.

The present invention is a technology to develop hybrid water-soluble drugs which otherwise are not water-soluble like, for example, paclitaxel, camptothecin, bexarotene, retinol etc. It is useful for in-vivo delivery of substantially water-insoluble drugs. The active molecule is hybridized with water-soluble molecules active or inactive in nature. The final formulation is ready-to-use after re-suspending in water for injection or any other compatible solutions.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "agent" refers to any molecule, compound, methodology and/or substance for use in the prevention, treatment, management and/or diagnosis of a disease or condition. As used herein, the term "effective amount" refers to the amount of a therapy that is sufficient to result in the prevention of the development, recurrence, or onset of a disease or condition, and one or more symptoms thereof, to enhance or improve the prophylactic effect(s) of another therapy, reduce the severity, the duration of a disease or condition, ameliorate one or more symptoms of a disease or condition, prevent the advancement of a disease or condition, cause regression of a disease or condition, and/or enhance or improve the therapeutic effect(s) of another therapy.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "therapeutic agent" refers to any molecule, compound, and/or substance that is used for the purpose of treating and/or managing a disease or disorder. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents (e.g., anti-cancer agents), chemotherapy, anti-angiogenic agents, and small molecule drugs (polyphenols or phenols).

As used herein, the terms "therapies" and "therapy" can refer to any method(s), composition(s), and/or agent(s) that can be used in the prevention, treatment and/or management of a disease or condition, or one or more symptoms thereof. In certain embodiments, the terms "therapy" and "therapies" refer to small molecule therapy.

As used herein, the terms "treat," "treatment," and "treating" in the context of the administration of a therapy to a subject refer to the reduction or inhibition of the progression and/or duration of a disease or condition, the reduction or amelioration of the severity of a disease or condition, such as cancer, and/or the amelioration of one or more symptoms thereof resulting from the administration of one or more therapies.

As used herein, the term "water-insoluble active agent" or "insoluble active agent" refers to an active agent having a solubility in water at 25° C. of less than 5 mg/ml, preferably below 1 mg/ml, and most preferably less than 0.1 mg/ml.

The term "synergistic" refers to, for example, two or more agents, e.g. a water-insoluble active agent and a complementary agent, when taken together, produce the same or greater therapeutic benefit is achieved using a combination therapy than by using any of the individual compounds alone. In some embodiments, the same or greater therapeutic benefit is achieved using a smaller amount (e.g., a lower dose or a less frequent dosing schedule) of a pharmaceutically active compound in a combination therapy than the amount generally used for individual therapy. Preferably, the use of a small amount of hybrid compound results in a reduction in the number, severity, frequency, or duration of one or more side-effects associated with the water-insoluble active agent alone. In various embodiments, treatment with the combination of the first and second agents may result in an additive, or even greater than additive, result compared to administration of either therapy alone. In some embodiments, a lower amount of each pharmaceutically active compound is used as part of a combination therapy compared to the amount generally used for individual therapy.

Complementary Agent

The complementary agent of the invention hybridizes with the substantially water-insoluble pharmacologically active agent and enhances the water solubility of the substantially water-insoluble pharmacologically active agent. An example of a hybridizing agent is curcumin.

Curcumin has the structure shown in (I)

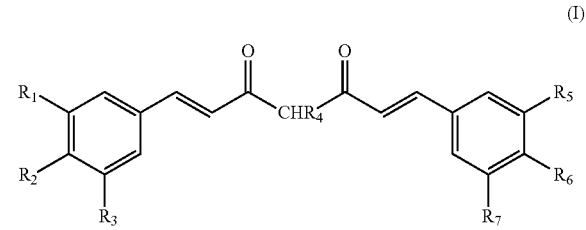

(I)

where R1 is —OCH3; R2 is —OH; R3 is —H; R4 is —H; R5 is —OCH3; R6 is —OH, and R7 is H. Curcumin has the chemical name (E, E) 1,7-bis(4-hydroxy-3-methoxypheny-1)-1,6-heptadiene-3,5-dione. In natural curcumin, the carbon-carbon double bonds are in the trans configuration.

Curcumin (diferuloylmethane) is a major active component of the food flavor, turmeric (*Curcuma longa*; S. Reddy S & B. B. Aggarwal, "Curcumin Is a Non-Competitive and Selective inhibitor of Phosphorylase Kinase," FEBS Lett. 341:19-22 (1994)). The anti-proliferative properties of curcumin in animals has been demonstrated by its inhibition of tumor initiation induced by benzo[a]pyrene and 7,12 dimethylbenz[a]anthracene (M. T. Huang et al., Carcinogenesis 13:2183-2186 (1992); M. A. Azuine & S. V. Bhide, Nutr. Cancer 17:77-83 (1992); M. A. Azuine & S. V. Bhide, Int. J. Cancer 51:412-415 (1992); M. Nagabhushan & S. V. Bhide, J. Am. Coll. Nutr. 11: 192-198 (1992)), and inhibition of populations of various cell types (H. P. Ammon & M. A. Wahl, Planta Med. 57:1-7 (1991); R. R. Satoskar et al., Int. J. Clin. Pharmacol. Res. 24:651-654 (1986); T. N. B. Shankar et al., Indian J. Exp. Biol. 18:73-75 (1980); R. Srivastava, Agents Action 38:298-303 (1989); H. C. Huang et al., Eur. J. Pharmacol. 221:381-384 (1992)). In addition, curcumin inhibits the tumor promotion caused by phorbol esters (M. T. Huang et al., Cancer Res. 48:5941-5946 (1988); A. H. Conney et al., Adv. Enzyme Regul. 31: 385-396 (1991); Y. P. Lu et al., "Effect of Curcumin on 12-O-Tetradecanoyl-phorbol-13-Acetate- and Ultraviolet B Light-Induced Expression of c-Jun and c-Fos in JB6 Cells and in Mouse Epidermis," Carcinogenesis 15: 2263-2270 (1994)). Recently, curcumin has been shown to inhibit pp60src (epidermal growth factor equivalent) tyrosine kinase via inhibition of phosphorylase kinase (S. Reddy & B. B. Aggarwal (1994), supra). It is possible that both the anti-tumor and anti-proliferative properties of curcumin may be mediated via its selective and non-competitive inhibition of phosphorylase kinase (S. Reddy & B. B. Aggarwal (1994), supra).

Curcumin is an inhibitor of Type I cyclic AMP-dependent protein kinase, the enzyme mainly responsible for activating phosphorylase kinase. The inhibition is competitive with respect to both ATP and the substrate (M. Hasmeda & G. M. Polya, "Inhibition of Cyclic AMP-Dependent Protein Kinase by Curcumin," Phytochemistry 42: 599-605 (1996)). Phosphorylase kinase, in turn, increases the migration of inflammatory cells, tumor cells, smooth muscle cells, and other cell types, as discussed above, as well as infectious organisms, increasing both the destructive and proliferative sequalae of the inflammatory response.

Also within the scope of the present invention is the use of curcumin derivatives or curcuminoids in place of curcumin itself or in addition to curcumin.

Among the curcuminoids that can be used in methods according to the present invention are curcuminoids of formula (I)

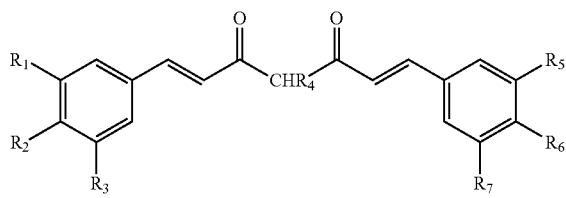

with the following alternative combinations of substituents:

(A) R1 is —H or —OCH3; R2 is —OH; R3 is —H; R4 is H; R5 is —H or OCH3; R6 is —OH, and R7 is —H, wherein only one of R1 and R5 is —OCH3;

(B) R1 is —H; R2 is —OH; R3 is —H or —OH; R4 is —H, R5 is —H; R6 is —OH; and R7 is —H or —OH;

(C) each of R1, R2, and R3 is —H, —OCH3, —OH, —ONa, acetyl, methyl, or ethyl; R4 is —H, —OH, ethyl, methyl, or acetyl; and each of R5, R6, and R7 is —H, —OCH3, —OH, —ONa, acetyl, methyl, or ethyl, wherein if R4 is —H or —OH, at least one of R2 and R6 is other than —H or —OH;

(D) R1 is —OH, R2 is —OH, R3 is —OH, R4 is —H or —OH, R5 is —OH, R6 is —OH; and R7 is —OH;

(E) R1 is —OCH3; R2 is —OCH3; R3 is —OCH3; R4 is —H or —OH; R5 is —OCH3; R6 is —OCH3; and R7 is —OCH3;

(F) R1 is —H; R2 is —OCH3; R3 is —OCH3; R4 is —H or —OH; R5 is —H; R6 is —OCH3; and R7 is —OCH3;

(G) R1 is —H; R2 is —OH; R3 is —H; R4 is —H; R5 is —H or —OH; R6 is —OH; and R7 is —H;

(H) R1 is —H; R2 is —OCH3; R3 is —H; R4 is —H; R5 is —H or —OH; R6 is —OCH3; and R7 is —H; or (I) R1 is —OH; R2 is —OCH3; R3 is —H or —OH; R4 is H or —OH; R5 is —OH; R6 is —OCH3; and R7 is —H or —OH.

Among the additional curcuminoids that can be used in methods according to the present invention are curcuminoids of formula (II):

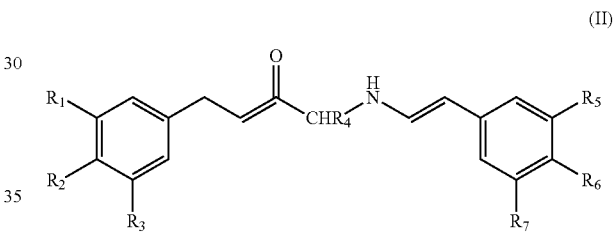

in which R1 through R7 can be as in curcumin or as in alternatives (A) through (1) above.

Also among the curcuminoids that can be used in methods according to the present invention are curcuminoids of formula (III):

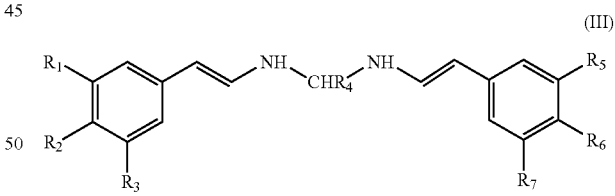

in which R1 through R7 can be as in curcumin or as in alternatives (A) through (I) above.

Additionally, among the curcuminoids that can be used in methods according to the present invention are analogues of curcuminoids of formulas (I) or (II) in which either or both of the oxygens of the carbonyl (CO) groups are replaced with sulfur to form a thiocarbonyl (CS) group.

Also among the curcuminoids that can be used in methods according to the present invention are furfural curcuminoid (formula IV) (X=—H); derivatives of furfural curcuminoid in which X is —OH, ethyl, methyl, or acetyl; salicyl curcuminoid (formula V) (X=—H), derivatives of salicyl curcuminoid in which X is —OH, ethyl, methyl, or acetyl; veratryl curcuminoid (formula VI) (X=—H); derivatives of veratryl curcuminoid in which X is —OH, ethyl, methyl, or acetyl; p-anisyl curcuminoid (formula VII) (X=—H); derivatives of p-anisyl curcuminoid in which X is —OH, ethyl, methyl, or acetyl; and piperonal curcuminoid (formula VIII) (X=—H); and derivatives of piperonal curcuminoid in which X is —OH, ethyl, methyl, or acetyl (R. J. Anto et al., "Antimutagenic and Anticarcinogenic Activity of Natural and Synthetic Curcuminoids," Mutation Res. 370: 127-131 (1996)). Additionally among the curcuminoids that can be used in methods according to the present invention are compounds that are analogues to the curcuminoids of formulas IV through VIII in which one or both of the carbonyl (CO) groups are replaced by amino (NH) groups in analogy with formulas II and III, or in which one or both of the oxygens of the carbonyl groups are replaced by sulfur to form thiocarbonyl groups.

Additionally among the curcuminoids that can be used in methods according to the present invention are tetrahydrocurcuminoids of formula IX produced by reducing curcuminoids by hydrogenation with a PtO2 catalyst, in which R1 through R7 can be as in curcumin or as in alternatives (A) through (I) above. Additionally among the curcuminoids that can be used in methods according to the present invention are compounds that are analogues to the curcuminoids of formula IX in which one or both of the carbonyl (CO) groups are replaced by amino (NH) groups in analogy with formulas II and III, or in which one or both of the oxygens of the carbonyl groups are replaced by sulfur to form thiocarbonyl groups.

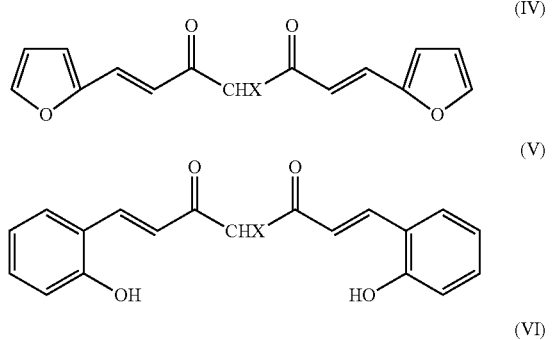

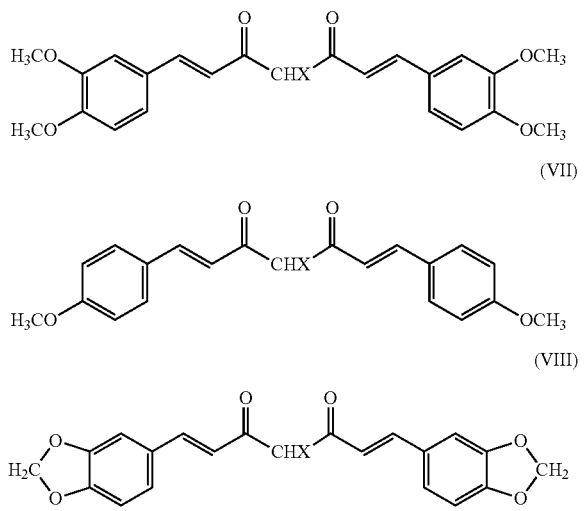

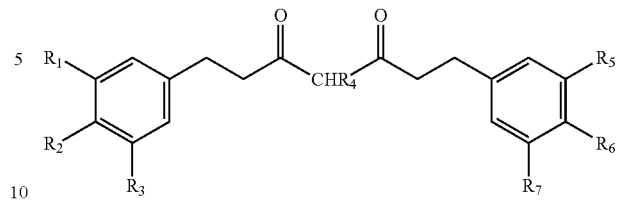

(T. Osawa et al., "Antioxidative Activity of Tetrahydrocurcuminoids," Biosci. Biotech. Biochem. 59:1609-1612 (1995)).

In natural curcumin, the stereochemistry at each of the double bonds is E (trans), so the molecule has the stereochemistry (E,E). However, the other geometrical isomers (Z,Z), (Z,E), and (E,Z), where these last two exist separately because of the nonsymmetric nature of the molecule, also can be prepared, and the use of these geometrical isomers is within the scope of the present invention. This includes the geometrical isomers of any of the molecules represented by Formulas I through IX, and recitation of these formulas in the specification and the claims of the present application includes both cis and trans geometrical isomers unless one of the geometrical isomers is explicitly specified.

Additionally, within the scope of the present invention are tautomers of the above structures in which one or both of the keto moieties located at the center portion of the molecule are replaced with enol moieties. These include the following: (1) molecules of Formula X in which in which R1 through R7 can be as in curcumin or as in alternatives (A) through (I) above; and (2) molecules of Formula XI in which R1 through R7 can be as in curcumin or as in alternatives (A) through (I) above. In Formulas X and XI, the double bonds are in the trans configuration, but also within the scope of the present invention are molecules in which one or more of the double bonds are in the cis configuration, as indicated above; for these formulas as well, their recitation in the specification and the claims of the present application includes both cis and trans geometrical isomers unless one of the geometrical isomers is explicitly specified. Additionally, among the curcuminoids that can be used in methods according to the present invention are analogues of curcuminoids according to formula (X) in which the carbonyl (CO) group is replaced with an amino (NH) group or in which the oxygen of the carbonyl group is replaced with a sulfur atom.

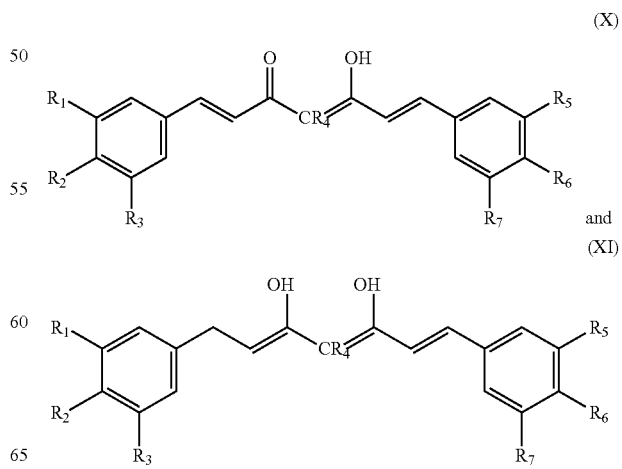

Additionally, within the scope of the present invention are reduced derivatives of curcumin represented by Formula XII in which R1 through R7 can be as in curcumin or as in alternatives (A) through (1) above.

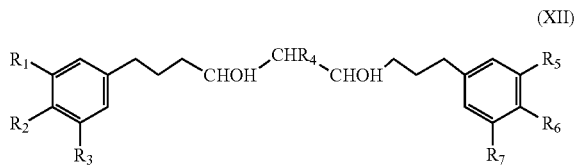

Also within the scope of the present invention are derivatives of curcumin or curcuminoids in which any of the methoxy groups are replaced with lower alkoxy groups such as ethoxy, n-propoxy, or isopropoxy. Additionally, within the scope of the present invention are derivatives of curcumin or curcuminoids in which any of the phenolic hydroxy groups in the structure are acylated with acyl substituents such as acetyl, propionyl, butyryl, or isobutyryl (Sreejayan & M. N. Rao, "Curcuminoids as Potent Inhibitors of Lipid Peroxidation," J. Pharm. Pharmacol. 46: 1013-1016 (1994)).

Also, additionally within the scope of the present invention are derivatives of curcumin or curcuminoids in which the hydrogens of one or more of the —OH groups present are replaced by an alkali metal, preferably sodium. When the hydrogens of the —OH groups in curcumin are replaced by sodium, the result is sodium curcuminate.

Active Agent

As used herein, "active agent" as includes an agent, drug, compound, composition of matter or mixture thereof which provides some pharmacologic, often beneficial, effect. The effect may be a therapeutic effect, such as a treatment effect or a prophylactic effect. This includes feeds, feed supplements, nutrients, drugs, vaccines, vitamins, and other beneficial agents. As used herein, "active agent" includes any physiologically or pharmacologically active substance that produces a localized or systemic effect in a patient. The active agent that can be delivered includes, for example, antibiotics, antifungal agents, antiviral agents, anepileptics, analgesics, anti-inflammatory agents, bronchodilators, and viruses and may be inorganic and organic compounds, including, without limitation, drugs which act on the peripheral nerves, adrenergic receptors, cholinergic receptors, the skeletal muscles, the cardiovascular system, smooth muscles, the blood circulatory system, synaptic sites, neuroeffector junctional sites, endocrine and hormone systems, the immunological system, the reproductive system, the skeletal system, autacoid systems, the alimentary and excretory systems, the histamine system and the central nervous system. Suitable agents may be selected from, for example, polysaccharides, steroids, hypnotics and sedatives, psychic energizers, tranquilizers, anticonvulsants, muscle relaxants, antiparkinson agents, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents (e.g., anti-cancer agents), chemotherapy, anti-angiogenic agents, and small molecule drugs.

Examples of active agents useful in this invention include but are not limited to Acemetacin, 5-aminosalicylic acid, Amiodarone, Amiodipine, Aspirin, Astemizole, Artemisinin, Aripiprazole, Ariprepitant, Azacitidine, Azathioprine, Azelasine, Azithromycin, Azithromycin dihydrate, Bacitracin, beta carotene, beta-sitosterol, Bexarotene Free Acid, Budesonide, Budesonide 98%, busulphan, Camphor, Camptothecin, Carmustine, Carvedilol, Capecitabine, Carbamazepine, Carbenicillin disodium salt, Cephalexin, Cefotaxime, Cilostazol, Clarithromycin, Celecoxib, Cisplatin, Clopidogrel Sulfate, Colchicine, Combrestastatin A4, Curcumin, Cyclosporin A, Daunorubicin hydrochloride, Dexamethasone, Diaminodiphenyl sulfone, Diclofenac, Dihydroergotamine Mesylate, Digoxin, Diindlylmethane,3,3, Docetaxel, Epothilone A, Erlotinib Monohydrochloride, β-Estradiol, Fexofenadine HCl, Griseofulvin, Ibuprofen, Itraconazole, Ivermectin, Lamotrigine, Lenalidomide, Leucovorin Calcium, Loperamide HCL, Loratadine, Magestrol Acetate, Methotrexate, Mevastatin, Naproxen, Nefedipine, Nystatin mycostatin, Nimodipine, Ofloxacin, Olanzapine, Paclitaxel, Paliperidone, Pomalidomide, Pravastatin Sodium, Prednisone, Quinine, Rapamycin, Resveratrol, Retinoic acid, Rifampin, Rlaxifene HCl, Statine, Sidenafil Citrate, Sildenafil Citrate >99%, sorafenib, Sulfasalazine, Tadalafil, Telaprevir, Temozolomide, Torisamide, Thalidomide, Valsartan, Valsartan 99%, Vardenafil hydrocholoride trihydrate, Variconazole, Zidovudine, Ziprasidone, Zoledronic acid, and Ziprasidone hydrochloride, and combinations thereof.

Examples of active agents useful in this invention include but are not limited to Acemetacin, Acetatamiprid, Alfacypermethrin, 5-aminosalicylic acid, Amiodarone, Amiodipine, Aspirin, Aprepitant, Artemisinin, Aripiprazole, 99%, Astemizole, Azacitidine (Vidaza), Azadirectin, Azathioprine, Azelastine, Azithromycin-dihydrate, Bacitracin, Beta Carotenene, Beta-sitosterol, Bexarotene, Free Acid (4), Budesonide, 98%, Busulphan, Camphor, Camptothecin, Cannabinoids, Carmustine, Carvedilol, Capecitabine, Carbamazepine, Carbenicillin disodium, Cephalexin, Cefotaxime, Celecoxib, Chlorfenapyr, Chlorantraniliprole, Cilostazol, Cisplatin, Clarithromycin, Clopidogrel Sulfate, Colchicine, CoQ10, Combrestastatin A4, Curcumin (2 cc.) for injection, Cyclophosphomide, Cyclosporin A, Cymoxanil, Daunorubicin hydrochloride, Dexamethasone, Diaminodiphenyl sulfone, 6-(2,3-Dichlorophenyl)-1,2,4-triazine-3, 5-diamine (Lamotrigine), Diclofenac, Dihydroergotamine Mesylate, Digooxin, Diindolylmethane,3,3, Docetaxel, Doxorubicin, Domperidone, Epothilone A, Escitalopram, Erlotinib Monohydrochloride, β-Estradiol, Etodolac, Etoposide, Famotidine, Fenazaquin, Fexofenadine hcl, Finasteride, Finofibrate, Fluconazole (candida), Fluticasone Propionate, Genistein, Griseofulvin, Ibuprofen, Indomethacin, Indoxacarb, Irbessartan (no EthOH), Itraconazole, Ivermectin, Lavamisloe, Lenalidomide, Leucovorin Calcium, Lidocaine, Loperamide HCL, Loratadine, Kaempferol, Ketoprofen, Magestrol Acetate, Mechlorethamine, Melphalan, Methotrexate, Mevastatin, Minimum 95% HPLC, Naproxen, Nebumelon, Nefedipine, Norfloxacin, Nystatin mycostatin, Nimodipine, Ofloxacin, Olanzapine, Opioid, Paclitaxel from Taxus Brevifolia, Paliperidone, Paracetamol, PCI-32765, Piroxicam, Pomalidomide, Pravastatin Sodium, Prethrin, Prednisone, Propanil pestanal, Pyrimethamine, Quinine, Rapamycin, Resveratrol, Retinoic acid 97%, Rifampin, Reloxifene hcl, Rosiglitazone, Saquinavir, Statine, Sidenafil Citrate >99%, Sorafenib, Sulcotrione, Sulfasalazine, Tadalafil (Cialis), Tebuconazole, Telaprevir, Temozolomide, Terbinafine, Tamoxifen, Thalidomide, Thiacloprid, Thiram, Torisamide, Triamcinolone, Tribenuron methyl, Valsartan 99%, Vardenafil hydrocholoride trihydrate, Variconazole, Vitamin D3, Zidovudine, Ziprasidone, Zoledronic acid, and combinations thereof.

Examples of active agents useful in this invention include but are not limited to paclitaxel, albumin-bound paclitaxel, docetaxel, bexarotene, all-trans-retinoic acid; actives for respiratory indications, such as bosentan, formoterol, loratidine, salmeterol, steroids and their salts, such as budesonide, testosterone, methyl testosterone, progesterone, dihydro epiandrosterone, medroxyprogesterone, estrogen, flunisolide, triamcinolone, beclomethasone, betamethasone, dexamethasone, fluticasone, fluticasone propionate, genistein, irbesartan mometasone, methylprednisolone, prednisone, hydrocortisone, and the like; peptides, such as cyclosporin and other water-insoluble peptides; retinoids, such as all cis-retinoic acid, all-trans-retinoic acid, 13-trans retinoic acid, retinoic acid 97%. and other vitamin A and beta carotene derivatives; vitamins D, D3, E, and K and water-insoluble precursors and derivatives thereof; prostagladins and leukotrienes and their activators and inhibitors including prostacyclin (epoprostanol), and prostaglandins E1 and E2; tetrahydrocannabinol, methadone, nicotine, amphetamine; lung surfactant lipids, lipid soluble antioxidants; anti-infective and chemotherapeutic drugs, such as acyclovir, adriamycin, albendazole, amphotericin B, amprenavir, azithromycin, cefdinir, ceftixime, ceftazidime, ciprofloxacin, clarithromycin, didanosine, dirithromycin, efavirenz, ganciclovir, gentamicin, intraconazole, itraconazole, ketoconazole, mefloquine, metronidazole, miconazole, nelfinavir, norfloxacin, ritonavir, saquinavir, tenofovir, voriconazole; CNS active agents, such as clozapine, clonazepam, entacapone, fluphenazine decanoate, fluvoxamine, imipramine, midazolam, olanzapine, paroxetine, sertraline, sulpiride, triazolam, zaleplon; ergotamine, dihydroergotamine, ergotamine tartrate, ergoloid, ergotamine fentanyl; triptans and their salts, such as sumatriptan, zolmitriptan, rizatriptan, naratriptan, eletriptan, almotriptan, frovatriptan, and the like; leukotriene receptor antagonists, such as zaflrlukast, montelukast, and zileuton; analgesics, such as celecoxib, diclofenac, ibuprofen, nabumetone, tramadol; active agents for cardiovascular indications, such as alendronate, amiodarone, candesartan, carvedilol, clopidogrel, clopidogrel sulfate, CoQ-10, curcumin (2 cc) for injection, diaminodiphenyl sulfone, dipyridamol, eposartan, felodipine, furosemide, isradipine, metolazone, propafenone, quinapril, ramipril, spironolactone, trandolapril, valsartan; statins, such as cerivistatin, pravastatin, simvastatin, fluvastatin, atorvastatin, lovastatin; actives used in oncology and immune suppression, such as azathioprin, carboplatin IV, cisplatin, docetaxel, epotoside, fluorouracil, irinotecan, letrozole, melphalan, mitotane, paclitaxel, pimecrolimus, sirolimus, tacrolimus, valrubicin; other actives: acutretin, aminogluthemide, amphetamine, atovaquone, baclofen, benezepril, benzonatate, bicalutanide, bupropion, busulphan, butenafine, calcifediol, calciprotiene, calcitriol, camptothecan, carbamezepine, carotene, chlorpheniramine, cholecalciferol, cilostazol, cimetidine, cinnarizine, cisapride, citrizine, clemastine, clomiphene, clomipramine, codeine, dantrolene, dexchlopheniramine, dicoumarol, digoxin, dihydrotachysterol, donepezil, dronabinol, ergocalciferol, ethinyl estradiol, etodolac, etoposide, danazol, famotidine, fenofibrate, fentanyl, fexofenadine, fexofenadine HCl, finasteride, fenofibrate, flucanazole, fluticasone propionate, flurbiprofen, follitropin, fosphenytion, furazolidone, gabapentin, gemfibrozil, glibenclamide, glipizide, glyburide, glymepride, griseofulvin, halofantrine, indomethacin, irbesartan, irbesartan (no EtOH), isosorbidedinatrate, isotretinoin, itraconazole, ivermectin, ketorolac, lamotrigine, 6-(2,3-dichlorophenyl)-1,2,4-triazine-3,5-diamine (lamotrigine), diindolylmethane,3,3, doxorubicin, domperidone, escitalopram, fenofibrate, kaempferol, ketoprofen, lansoprazole, lavamisloe, lenalidomide, leflunomide, Lidocaine, lisinopril, loperamide, loperamide HCl, loratadine, L-thryroxine, mechlorethamine mefepristone, megestrol, methoxsalen, miglitol, minoxidil, mitoxantrone, modafinil nimodipine, nalbuphine, nebumeton, nebumelon, nystatin mycostatin, nifedipine, nilsolidipine, nilutanide, nimodipine, nitrofurantoin, nizatidine, ofloxacin, olanzopine, omeprazole, oprevelkin, osteradiol, oxaprozin, paclitaxel, paclitaxel from *Taxus Brevifola*, paracetamol, PCI-32765, piroxicam, paricalcitol, pentazocine, pioglitazone, pizofetin, probucol, propofol, pseudo-ephedrine, pyridostigmine, pyrimethamine, rabeprazole, raloxifene, raloxifene HCl, refocoxib, repaglinide, rifabutine, rifapentine, rimexolone, rosigiltazone, sibutramine, sildenafil, tacrine, tamoxifen, tamsulosin, targretin, tazarotene, telmisartan, teniposide, terbinafine, terzosin, thalidomide, tiagabine, ticlidopine, tirofibran, tizanidine, topiramate, topotecan, toremifene, tretinoin, troglitazone, trovafloxacin, venlafaxine, vertoporfin, vigabatrin, zolpidem, zopiclone, and combinations thereof. The active agents may be in various forms, such as charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted.

The active agent of the present invention may be combined with pharmaceutical carriers or excipients. Such carriers or excipients may serve simply as bulking agents when it is desired to reduce the active agent concentration in the powder which is being delivered to a patient, or may be added to the active agent prior to processing for taste masking and/or to improve the stability and/or dispersibility of the powder. In other embodiments, the excipients may be delivered via the pulmonary route without an active agent, for example in clinical trials as a placebo. Such excipients include but are not limited to (a) carbohydrates, e.g., monosaccharides such as fructose, galactose, glucose, D-mannose, sorbose, and the like; disaccharides, such as lactose, trehalose, cellobiose, and the like; cyclodextrins, such as 2-hydroxypropyl-.beta.-cyclodextrin; and polysaccharides, such as raffinose, maltodextrins, dextrans, and the like; (b) amino acids, such as alanine, praline, glycine, arginine, aspartic acid, glutamic acid, cysteine, lysine, leucine, trileucine and the like; (c) organic salts prepared from organic acids and bases, such as sodium citrate, sodium ascorbate, magnesium gluconate, sodium gluconate, tromethamine hydrochloride, and the like; (d) peptides and proteins such as aspartame, human serum albumin, gelatin, and the like; (e) alditols, such as mannitol, xylitol, and the like; (f) biodegradable polymers such as polyvinylpyrrolidone or cellulose derivatives, and (g) surfactants including fluorinated and nonfluorinated compounds such as saturated and unsaturated lipids, nonionic detergents, nonionic block copolymers, ionic surfactants and combinations thereof. A preferred group of excipients includes lactose, trehalose, raffinose, maltodextrins, glycine, alanine, proline, leucine, tri-leucine, sodium citrate, human serum albumin, mannitol, and phospholipids from both natural and synthetic sources that preferably have a gel to liquid crystal phase transition greater than about 40° C. Preferred phospholipids are relatively long chain (i.e. C16-C22) saturated lipids and more preferably comprise saturated phospholipids, most preferably saturated phosphatidylcholines having acyl chain lengths of 16:0 or 18:0 (palmitoyl and stearoyl). Exemplary phospholipids include phosphoglycerides such as dipalmitoylphosphatidylcholine, disteroylphosphatidylcholine, diarachidoylphosphatidylcholine, dibehenoylphosphatidylcholine, diphosphatidyl glycerol, short-chain phosphatidylcholines, long-chain saturated phosphatidylethanolamines, long-chain saturated phosphatidylserines, long-chain saturated phosphatidylglycerols, aspirin, camptothecin, resveratrol, statin, poly-phenols, phenols, lectins and long-chain saturated phosphatidylinositols.

Polymer

A polymer of the invention is, for example, selected from a group which is soluble in alcohol as well as in water. The polymer of the invention is, for example, water-soluble polymer. Water-soluble polymers are selected from but not limited to methylcellulose, hydroxyethyl cellulose, hydroxypropyl cellulose, hydroxypropyl methylcellulose, hydroxypropyl ethylcellulose, sodium carboxymethylcellulose, polyvinyl alcohol, polyvinylpyrrolidone, polyethylene glycol, poly(methyl methacrylate), polycarbophil, gelatin, alginate, poly(acrylic acid), polyethylene oxide and chitosan or a derivative thereof.

Examples of the water-soluble polymers include, for example, hydroxymethyl cellulose, hydroxyethyl cellulose, hypromellose having a molecular weight of 1,000 to 4,000,000, hydroxypropyl cellulose having a molecular weight of 2,000 to 2,000,000, carboxyvinyl polymers, chitosans, mannans, galactomannans, xanthans, carageenans, amylose, alginic acid, salts and derivatives thereof, pectin, acrylates, methacrylates, acrylate/methacrylate copolymers, polyacid anhydrides, polyamino acids, poly(methylvinyl ether/maleic anhydride) polymers, polyvinyl alcohols, glucans, scleroglucans, carboxymethyl cellulose and derivatives thereof, ethyl cellulose, methyl cellulose, or conventional water-soluble cellulose derivatives. Hypromellose having a molecular weight of 3,000 to 2,000,000 is preferable. The content of the water-soluble polymer in the layer 1 or the layer 3 is generally 5 to 90 W/W %, preferably 10 to 85 W/W %, more preferably 20 to 80 W/W %, with respect to the weight of each layer. The content of the water-soluble polymer in the layer 2 is generally 5 to 90 W/W %, preferably 10 to 85 W/W %, to the weight of the layer.

The water-soluble polymer carrier may include any carriers as long as it may be commonly used for improving solubility of a poorly soluble drug. According to one embodiment of the invention, it may include pharmaceutically acceptable water-soluble polymer, specifically one or more selected from the group consisting of hydroxypropylmethylcellulose (HPMC, for example, those having weight average molecular weight of about 10,000 to 1,500,000), polyethyleneglycol (PEG, for example, those having weight average molecular weight of 3,000 to 9,000), polyvinylpyrrolidone (PVP, for example, those having weight average molecular weight of 2,500 to 2,500,000), cellulose, and a combination thereof, more specifically, HPMC.

In a preferred embodiment, the polymer is PVP.

According to one embodiment of the invention, the weight ratio of the poorly soluble drug and the polymer may be 1:1 to 1:15, preferably 1:1 to 1:10, most preferably 1:1 to 1:5.

Hybrid Drug

As used herein, the term "hybrid drug" means that the water-insoluble active agent, complementary agent, and polymer are linked by, for example, by ionic bonds, physical forces such van der Waals or hydrophobic interactions, hydrogen bonds, encapsulation, embedding, and/or combinations thereof. In an exemplary embodiment, the polymer acts as a bridge between the water-insoluble active agent and the complementary agent.

The compositions and methods of the invention are useful for the in vivo delivery of substantially water-insoluble drugs, like taxol. The use of specific composition and preparation conditions enables the reproducible production of unusually water-soluble hybrid drug formulation, which can be sterile-filtered. The hybrid drug system produced according to the invention can be converted into a redispersible dry powder comprising nanoparticles of drug and drugs. This results in a unique delivery system, in which part of the pharmacologically active agent is readily bioavailable. The present invention is useful for in vivo delivery of substantially water-insoluble drugs. The active molecule is hybridized with water-soluble molecules active or inactive in nature. The final formulation is ready-to-use after re-suspending in water for injection or any other compatible solutions.

Nanoparticle

The term "nanoparticles" as used herein describes particles having an average diameter of between about 1 nanometer (nm) and about 1000 nm. Nanoparticles of a particular molecular entity or compound exhibit physico-chemical properties that are significantly different from that of larger forms of the same molecular entity or compound. Preferably, the nanoparticles of the present invention have a diameter of about 100 nm or less, more preferably less than 50 nm, and even more preferably less than about 30 nm.

"Nanoparticles" are solid particles of an average particle diameter of, for example, less than about 1 micron (micrometer). One micron is 1,000 nanometers (nm).

"Stabilized" nanoparticles are nanoparticles coated with a stabilizing material and having a reduced tendency for aggregation and loss of dispersion with respect to nanoparticles of the compound of the invention without a stabilizing coating.

A nano-spray is a spray containing nanoparticles or a spray that produces nanoparticles. A nanodispersion is a dispersion containing nanoparticles. A nanosuspension is a suspension containing nanoparticles.

In certain non-limiting embodiments, pharmaceutical compositions may comprise, for example, at least about 0.1% of an active ingredient or nanoparticles, composite nanoparticles, or nanocapsules, for example. In other embodiments, the an active ingredient or nanoparticles, composite nanoparticles, or nanocapsules may comprise between about 2% to about 75% of the weight of the unit, or between about 25% to about 60%, for example, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered.

In order to increase the effectiveness of a treatment with the nanoparticles, nanogels, composite nanoparticles, nanosuspension, or nanocapsules of the present invention, it may be desirable to combine these nanoparticles, composite nanoparticles, or nanocapsules with other therapies effective in the treatment of a particular disease or condition.

The diameter size of the nanoparticles present in the redispersable powder or in the aqueous dispersion can be ascertained by light scattering measurements, for example using a dynamic light scattering instrument, such as the Zetasizer Nano ZS (Malvern Instruments, UK). The particle size can be determined either by volume distribution or by number distribution. The methods described herein generally yield nanoparticles of diameter less than 500 nm. The nanoparticles can be of diameter in the range 400 to 500 nm, 300 to 400 nm, 200 to 300 nm, 100 to 200 nm, 50 to 100 nm, 10 to 50 nm or 1 to 5 nm. In specific embodiments of the methods and of the redispersible powder disclosed herein, the nanoparticles have a diameter of less than about 100 nm, preferably less than about 50 nm, more preferably less than about 30 nm, and more preferably in the range of about 5 to about 50 nm. The microemulsion droplets are typically below 30 nm in diameter.

The nanoparticles present in the redispersible powder or in the aqueous dispersion of the invention are in a particulate form. This means that the nanoparticles are discrete, individual, non-aggregated particle entities composed of a water-insoluble organic compound, such that the water-insoluble organic compound is not enclosed within, incorporated within, embedded within, contained within or associated with any encapsulation form, bead, carrier, matrix or similar delivery agent.

In specific embodiments of the methods of the invention and of the redispersible powder, the nanoparticles comprise at least about 50% by weight of the water-insoluble organic compound. In other embodiments, the nanoparticles comprise at least about 80% by weight of the water-insoluble organic compound. In other embodiments, the nanoparticles consist essentially of the water-insoluble organic compound. In a specific embodiment of the method for preparing a redispersible powder, the nanoparticles comprise at least about 5% of the redispersible powder. In a specific embodiment of the method for preparing an aqueous dispersion, the nanoparticles comprise at least about 0.5% of the aqueous dispersion. In another embodiment, the nanoparticles comprise at least about 5.0% of the aqueous dispersion.

In specific embodiments of the methods of the invention and of the redispersible powder, the active molecule is present at 0.05%-90% of the total weight of the powder.

The methods of the invention described herein provide nanoparticles of a water-insoluble organic compound, which have significantly increased solubility and dissolution rate as compared to the same compound in unprocessed form, i.e., in a form which has not undergone any particle size reduction or other treatment to increase its solubility or dissolution rate. This is highly advantageous for the preparation of diverse consumer products, in which the active agents or other important components are usually insoluble or at best, poorly soluble. Thus, manufacturing and delivery solutions can be provided for example, for pharmaceutical compositions comprising poorly soluble drugs; for agricultural compositions e.g., poorly soluble pesticides, processed foods comprising poorly soluble preservatives, and cosmetics comprising poorly soluble active ingredients. The invention provides a means of providing such compounds at relatively high concentrations, compared to unprocessed forms, and also provides synergistic effects.

Thus, in one embodiment, the solubility of the water-insoluble organic compound is at least about 5-90 times greater than the solubility of the water-insoluble organic compound in unprocessed form—i.e. not in the form of the nanoparticles prepared by the invention. In another embodiment, the solubility of the water-insoluble organic compound is at least about 10 times greater than the solubility of the water-insoluble organic compound in unprocessed form.

In another embodiment, the dissolution rate of the nanoparticles is at least about 5 times greater than the dissolution rate of the water-insoluble organic compound in unprocessed form. In yet another embodiment, the dissolution rate of the nanoparticles is at least about 10-90 times greater than the dissolution rate of the water-insoluble organic compound in unprocessed form.

Thus, for example, if one milligram of a water-insoluble organic compound requires five minutes to dissolve, only one minute is required for the nanoparticles, at the same concentration. In addition, the solubility (gram material to gram water) also increases upon decreasing the size of the particles.

In specific embodiments, the water-insoluble organic compound is in an amorphous or a partially amorphous form. Amorphous forms may have increased solubility relative to non-amorphous forms. Using amorphous forms of poorly soluble molecules can be a real advantage. Amorphous materials usually show a significantly higher solubility than their crystalline counterparts, have higher dissolution rate and, in case of drug entities, higher bioavailability in vivo. X-ray diffraction measurements and differential scanning calorimetry (DSC) measurements can be performed on the nanoparticles to reveal the presence of amorphous or crystalline materials.

In one embodiment of the method for preparing a redispersible powder, the process further comprises the step of crystallizing the nanoparticles thereby providing crystalline nanoparticles. In another embodiment, the crystallizing is carried out by aging the nanoparticles. X-ray diffraction measurements can be performed on the nanoparticles to reveal crystallinity.

Solvents

There are no specific limitations with respect to the organic solvent employed in the method of the invention. Suitable solvents include, for example, alcohols, such as, methanol, ethanol, n-propanol, 2-propanol, n-butanol, 2-butanol, C1-C4 linear or branched alcohol; aromatic hydrocarbon, such as, benzene, toluene, and xylene, substituted toluenes, substituted xylenes; halogenated hydrocarbons, such as, dichloromethane, dichloroethane, trichloroethane, tetrachloroethane, dichloropropane, chloroform, carbon tetrachloride; ethers, such as, diethyl ether, diisopropyl ether, tert-butyl methyl ether, dioxane, tetrahydrofuran; ketones, such as, acetone, methyl ethyl ketone, methyl isobutyl ketone; alkyl acetate, such as, ethyl acetate, n-propyl acetate, isopropyl acetate, n-butyl acetate, isobutyl acetate; alkyl nitriles, such as, acetonitrile, propionitrile; amides, such as, N,N-dimethylformamide; dimethyl sulfoxide. Preferred are alcohols. More preferred is methanol, ethanol or 2-propanol. The organic solvents may be employed singly or in combination. In a preferred embodiment, the solvents are 1-4 carbon alcohols.

Formulations

The compounds of the invention may be administered enterally or parenterally. Mixed with pharmaceutically suitable auxiliaries, e.g., as described in the standard reference, Gennaro et al., Remington's Pharmaceutical Sciences. The compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray.

For making dosage units, e.g., tablets, the use of conventional additives such as fillers, colorants, polymeric binders and the like is contemplated. In general, any pharmaceutically acceptable additive which does not interfere with the function of the active compounds can be used. Suitable carriers with which the compositions can be administered include lactose, starch, cellulose derivatives and the like, or mixtures thereof, used in suitable amounts.

Dosage Forms

The compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage. These forms are well known in the art and are packaged appropriately. The compositions can be formulated for oral, nasal, buccal, ocular, urethral, transmucosal, vaginal, topical or rectal delivery.

The pharmaceutical composition can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water-soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: 1. resistance to dissolution and disintegration in the stomach; 2. impermeability to gastric fluids and drug/carrier/enzyme while in the stomach; 3. ability to dissolve or disintegrate rapidly at the target intestine site; 4. physical and chemical stability during storage; 5. non-toxicity; 6. easy application as a coating (substrate friendly); and 7. economical practicality.

Dosage forms of the compositions of the present invention can also be formulated as enteric coated delayed release oral dosage forms, i.e., as an oral dosage form of a pharmaceutical composition as described herein which utilizes an enteric coating to affect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers for use in the present invention are anionic carboxylic polymers.

Shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

In carrying out the method of the present invention, the combination of the invention may be administered to mammalian species, such as dogs, cats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfite) or the like.

The dose administered must be carefully adjusted according to age, weight and condition of the patient, as well as the route of administration, dosage form and regimen and the desired result.

The pharmaceutical compositions of the invention may be administered in the dosage forms in single or divided doses of one to four times daily. It may be advisable to start a patient on a low dose combination and work up gradually to a high dose combination.

Tablets of various sizes can be prepared, e.g., of about 1 to 2000 mg in total weight, containing one or both of the active pharmaceutical ingredients, with the remainder being a physiologically acceptable carrier of other materials according to accepted pharmaceutical practice. These tablets can be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonful.

Dosage forms can be administered to the patient on a regimen of, for example, one, two, three, four, five, six, or other doses per day In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, *acacia*, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

One embodiment of this invention includes methods of treating, preventing, or diagnosing a particular disease or condition by administering the disclosed nanoparticles, composite nanoparticles, nanosuspension, or nanocapsules to a subject. In many instances, the nanoparticles, composite nanoparticles, or nanocapsules are administered alone or can be included within a pharmaceutical composition. An effective amount of a pharmaceutical composition, generally, is defined as that amount sufficient to ameliorate, reduce, minimize, or limit the extent of the disease or condition. More rigorous definitions may apply, including elimination, eradication, or cure of the disease or condition.

"Nanoparticles" are solid particles of an average particle diameter of, for example, less than about 1 micron (micrometer). One micron is 1,000 nanometers (nm).

"Stabilized" nanoparticles are nanoparticles coated with a stabilizing material and having a reduced tendency for aggregation and loss of dispersion with respect to nanoparticles of the compound of the invention without a stabilizing coating.

A nano-spray is a spray containing nanoparticles or a spray that produces nanoparticles. A nanodispersion is a dispersion containing nanoparticles. A nanosuspension is a suspension containing nanoparticles.

The liquid formulations useful herein may comprise a solvent, solution, suspension, microsuspension, nanosuspension, emulsion, microemulsion, gel or even a melt containing the active component or components. In some embodiments the nanoparticles, nanofibers, or nanofibrils may be in the form of, or within or on, granules, powders, suspensions, solutions, dissolvable films, mats, webs, tablets, or releasable forms particularly releasable dosage forms. Other particular useful forms are concentrates to which a diluting liquid is added prior to use. The product may also be sprayed onto the inner surface of a container to which a liquid is added later prior to use and the nanoparticles, nanofibers, or nanofibrils, are released into the liquid.

Topical formulations are a preferred embodiment of the present invention. Topical formulations may take any suitable form. In general, it is preferred that they exhibit some level of viscosity, in order that they can be targeted at the desired area without running off. Accordingly, it is generally preferred to formulate the compositions of the invention as creams, gels, ointments, and patches.

Poloxamers may be used in preferred formulations of the present invention. They are co-polymers which consist of a hydrophobic poloxypropylene (POP) molecule sandwiched between two hydrophilic molecules of poloxyethylene (POE).

Oils may also be used in the present invention. Prior to administration, a vehicle, such as polyoxyethylated castor oil, is normally diluted with saline to form the emulsion. Buccal formulations may also be employed. Transmucosal delivery of therapeutic agents is a popular administration form, because mucous membranes are relatively permeable, allowing for the rapid uptake of a drug into the systemic circulation and avoiding first pass metabolism. Transmucosal products can be designed to be administered via the nasal route and oral/buccal route using mucoadhesives. In the development of these drug delivery systems, mucoadhesion of the device/formulation is a key element. The term 'mucoadhesive' is commonly used for materials that adhere to the mucin layer of a biological membrane. Mucoadhesive polymers have been utilized in many different dosage forms in efforts to achieve systemic and localized delivery of drugs through the different mucosae. These dosage forms include tablets, patches, tapes, films, semisolids and powders. To serve as mucoadhesive polymers, the polymers should possess physicochemical features such as being predominantly anionic with numerous hydrogen bond-forming groups, suitable surface properties for wetting mucus/mucosal tissue surfaces and sufficient flexibility and length (molecular weight) to penetrate the mucus network or tissue crevices. Diverse classes of polymers have been reported as potential mucoadhesives such as carbomers (polyacrylic acids), hydroxypropyl methylcellulose (HPMC) as well as naturally occurring polymers, such as hyaluronic acid and chitosan.

Preparation of suitable formulations is within the skill of those in the art, and suitable excipients for inclusion in any such formulation include, for example, gellants, viscosifiers, penetration enhancers, preservatives, such as antibiotics and antifungals, and cosmetic ingredients, such as scents and colorings.

Suitable gelling agents include: water soluble cellulose derived polymers, such as hydroxyalkyl cellulose polymers (e.g. hydroxymethylcellulose, hydroxyethylcellulose, hydroxypropylcellulose and hydroxypropylmethylcellulose), carboxymethyl cellulose, methylhydroxyethyl cellulose and methyl cellulose, carbomer (e.g. carbopol); and carrageenans. The gelling agent may be added in any suitable amount, such as 1-5% (w/w). Preferred gelling agents are cellulose derived, most preferably hydroxyalkylcellulose, particularly hydroxyethylcellulose.

Suitable preservatives will be apparent to those skilled in the art, and include the parabens (methyl, ethyl, propyl and butyl), benzoic acid and benzyl alcohol. Preservatives employed solely for that purpose will generally form 1% (w/w) or less of the final topical formulation.

Suitable penetration enhancers include isopropyl alcohol, sulphoxides (such as dimethylsulphoxide, DMSO), Azones (e.g. laurocapram), pyrrolidones (for example 2-pyrrolidone), alkanols (e.g. decamp, and glycols (for example propylene glycol).

Pharmaceutical compositions of the present invention can include nanoparticles, composite nanoparticles, nanosuspension, or nanocapsules of the present invention.

In certain non-limiting embodiments, pharmaceutical compositions may comprise, for example, at least about 0.1% of an active ingredient or nanoparticles, composite nanoparticles, or nanocapsules, for example. In other embodiments, the an active ingredient or nanoparticles, composite nanoparticles, or nanocapsules may comprise between about 2% to about 75% of the weight of the unit, or between about 25% to about 60%, for example, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered.

The composition may also include various antioxidants to retard oxidation of one or more active ingredient or nanoparticles, composite nanoparticles, nanosuspension, or nanocapsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof). In a preferred embodiment, the complementary molecule of hybrid drug is of antioxidant and antimicrobial nature.

In order to increase the effectiveness of a treatment with the nanoparticles, nanogels, composite nanoparticles, nanosuspension, or nanocapsules of the present invention, it may be desirable to combine these nanoparticles, composite nanoparticles, or nanocapsules with other therapies effective in the treatment of a particular disease or condition.

The formulations as described above may be administered for a prolonged period, that is, for as long as the potential for a disease or condition remains or the symptoms continue.

Packaging/Treatment Kits

The present invention relates to a kit for conveniently and effectively carrying out the methods in accordance with the present invention. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose; or an AM dose is packaged with a PM dose. Alternatively, placebo dosages, or vitamin or dietary supplements, either in a form similar to or distinct from the pharmaceutical active dosages, can be included.

In one aspect, the package, kit or container comprises a "blister package" (also called a blister pack, or bubble pack). In one aspect, the blister package consists two or more separate compartments: Am dosage of this invention, and PM dosage of this invention, or mid-day dosage of this invention. This blister package is made up of two separate material elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising a composition (e.g., a (the multi-ingredient combination of drugs of the invention) combination of active ingredients) of the invention. Blister packs, clamshells or trays can be designed to be non-reclosable, so consumers can tell if a package has already opened. They are used to package for sale goods where product tampering is a consideration, such as the pharmaceuticals of the invention. In one aspect, a blister pack of the invention comprises a moulded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one aspect, a specialized form of a blister pack is a strip pack.

In one aspect, a blister pack also comprises a method of packaging where the compositions comprising combinations of ingredients of the invention are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the invention are used, and they can comprise of two vacuum-formed PVC sheets meshed together at the edges, with the informative card inside.

In one aspect, blister packaging comprises at least two components (e.g., is a multi-ingredient combination of drugs of the invention): a thermoformed "blister" which houses the product (e.g., a pharmaceutical combination of the invention), and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or large. Conventional blister packs can also be sealed (e.g., using an AERGO 8 DUO®, SCA Consumer Packaging, Inc., DeKalb, Ill.) using regular heat seal tooling. This alternative aspect, using heat seal tooling, can seal common types of thermoformed packaging.

As discussed herein, the products of manufacture of the invention can comprise the packaging of the therapeutic drug combinations of the invention, alone or in combination, as "blister packages" or as a plurality of packettes, including as lidded blister packages, lidded blister or blister card or packets, or a shrink wrap.

In one aspect, laminated aluminum foil blister packs are used, e.g., for the preparation of drugs designed to dissolve immediately in the mouth of a patient. This exemplary process comprises having the drug combinations of the invention prepared as an aqueous solution(s) which are dispensed (e.g., by measured dose) into an aluminum (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual 'push-through' blister packs/packettes are used, e.g., using hard temper aluminum (e.g., alufoil) lidding material. In one aspect, hermetically-sealed high barrier aluminum (e.g., alufoil) laminates are used. In one aspect, any of the invention's products of manufacture, including kits or blister packs, use foil laminations and strip packs, stick packs, sachets and pouches, peelable and non-peelable laminations combining foil, paper, and film for high barrier packaging.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

The invention will be illustrated in more detail with reference to the following Examples, but it should be understood that the present invention is not deemed to be limited thereto.

EXAMPLES

Example 1—Hybrid Paclitaxel

This example provides formulations of hybrid paclitaxel. Briefly, paclitaxel is dissolved in an organic solvent, such as ethanol in a separate container, and the solution is added to another solution of curcumin, curcuminoid, or curcumin derivative is selected from the group consisting of: (a) curcumin; (b) a curcuminoid of formula (I) in which: (i) $R_1$ is —H or —OCH$_3$; $R_2$ is —OH; $R_3$ is —H; $R_4$ is H; $R_5$ is —H or OCH$_3$; $R_6$ is —OH, and $R_7$ is —H, wherein only one of $R_1$ and $R_5$ is —OCH$_3$; (ii) $R_1$ is —H; $R_2$ is —OH; $R_3$ is —H or —OH; $R_4$ is —H, $R_5$ is —H; $R_6$ is —OH; and $R_7$ is —H or —OH; (iii) each of $R_1$, $R_2$, and $R_3$ is —H, —OCH$_3$, —OH, —ONa, acetyl, methyl, or ethyl; $R_4$ is —H, —OH, ethyl, methyl, or acetyl; and each of $R_5$, $R_6$, and $R_7$ is —H, —OCH$_3$, —OH, —ONa, acetyl, methyl, or ethyl, wherein if $R_4$ is —H or —OH, at least one of $R_2$ and $R_6$ is other than —H or —OH; (iv) $R_1$ is —OH, $R_2$ is —OH, $R_3$ is —OH, $R_4$ is —H or —OH, $R_5$ is —OH, $R_6$ is —OH; and $R_7$ is —OH; (v) $R_1$ is —OCH$_3$; $R_2$ is —OCH$_3$; $R_3$ is —OCH$_3$; $R_4$ is —H or —OH; $R_5$ is —OCH$_3$; $R_6$ is —OCH$_3$; and $R_7$ is —OCH$_3$; (vi) $R_1$ is —H; $R_2$ is —OCH$_3$; $R_3$ is —OCH$_3$; $R_4$ is —H or —OH; $R_5$ is —H; $R_6$ is —OCH$_3$; and $R_7$ is —OCH$_3$; (vii) $R_1$ is —H; $R_2$ is —OH; $R_3$ is —H; $R_4$ is —H; $R_5$ is —H or —OH; $R_6$ is —OH; and $R_7$ is —H; (viii) $R_1$ is —H; $R_2$ is —OCH$_3$; $R_3$ is —H; $R_4$ is —H; $R_5$ is —H or —OH; $R_6$ is —OCH$_3$; and $R_7$ is —H; or (ix) $R_1$ is —OH; $R_2$ is —OCH$_3$; $R_3$ is —H or —OH; $R_4$ is H or —OH; $R_5$ is —OH; $R_6$ is —OCH$_3$; and $R_7$ is —H or —OH; in ethanol in a separate container. These components are mixed thoroughly until a uniform preparation is ready. A suitable amount of another polymer is added to complete the reaction. The mixture is homogenized for 10 minutes at low RPM to form a crude emulsion, and then transferred into a high pressure homogenizer. The preparation is sonicated for 20 minutes to complete the reaction and formation of nanoparticles. The resulting system is transferred into a rotary evaporator, and the organic solvent is rapidly removed at 40° C., at reduced pressure (30 mm Hg) for 20-30 minutes. The dispersion is then further lyophilized for 48 hours. The resulting cake can be easily reconstituted to the original dispersion by addition of sterile water or saline, which may contain antimicrobial agent(s).

Exemplary formulations of compositions that can be prepared are provided below (only concentrations of paclitaxel, are provided):

Formulation 1: 5 mg in ethanol paclitaxel; 10 mg/ml $2^{nd}$ partner in ethanol; 25 mg polymer Formulation 2 500 mg paclitaxel; 1000 mg of $2^{nd}$ partner; 2.5 gram of polymer Formulation 3: 5 mg/ml paclitaxel; 56 mg/ml human albumin; 0.5 mg/ml potassium sorbate Result: The product has been made in small quantity using regular pilot scale and regular laboratory equipment.

Testing: water solubility of the drug formulation has been tested with spectrophotometer and microscopic observation and pictures of the same has been attached.

Activity: activity of the drug formulation has been test in tissue culture using cancer cell line like BxPc and SKOV and normal cell line. In SKOV the activity of the drug formulation in SKOV is more than 50% higher. See FIG. 1.

Example 2—Docetaxel Hybrid

Water-soluble docetaxel hybrid drug is prepared to dissolve 500 mg of docetaxel into 1 gram of $2^{nd}$ partner selected from the group consisting of: (a) curcumin; (b) a curcuminoid of formula (I) in which: (i) $R_1$ is —H or —OCH$_3$; $R_2$ is —OH; $R_3$ is —H; $R_4$ is H; $R_5$ is —H or OCH$_3$; $R_6$ is —OH, and $R_7$ is —H, wherein only one of $R_1$ and $R_5$ is —OCH$_3$; (ii) $R_1$ is —H; $R_2$ is —OH; $R_3$ is —H or —OH; $R_4$ is —H, $R_5$ is —H; $R_6$ is —OH; and $R_7$ is —H or —OH; (iii) each of $R_1$, $R_2$, and $R_3$ is —H, —OCH$_3$, —OH, —ONa, acetyl, methyl, or ethyl; $R_4$ is —H, —OH, ethyl, methyl, or acetyl; and each of $R_5$, $R_6$, and $R_7$ is —H, —OCH$_3$, —OH, —ONa, acetyl, methyl, or ethyl, wherein if $R_4$ is —H or —OH, at least one of $R_2$ and $R_6$ is other than —H or —OH; (iv) $R_1$ is —OH, $R_2$ is —OH, $R_3$ is —OH, $R_4$ is —H or —OH, $R_5$ is —OH, $R_6$ is —OH; and $R_7$ is —OH; (v) $R_1$ is —OCH$_3$; $R_2$ is —OCH$_3$; $R_3$ is —OCH$_3$; $R_4$ is —H or —OH; $R_5$ is —OCH$_3$; $R_6$ is —OCH$_3$; and $R_7$ is —OCH$_3$; (vi) $R_1$ is —H; $R_2$ is —OCH$_3$; $R_3$ is —OCH$_3$; $R_4$ is —H or —OH; $R_5$ is —H; $R_6$ is —OCH$_3$; and $R_7$ is —OCH$_3$; (vii) $R_1$ is —H; $R_2$ is —OH; $R_3$ is —H; $R_4$ is —H; $R_5$ is —H or —OH; $R_6$ is —OH; and $R_7$ is —H; (viii) $R_1$ is —H; $R_2$ is —OCH$_3$; $R_3$ is —H; $R_4$ is —H; $R_5$ is —H or —OH; $R_6$ is —OCH$_3$; and $R_7$ is —H; or (ix) $R_1$ is —OH; $R_2$ is —OCH$_3$; $R_3$ is —H or —OH; $R_4$ is H or —OH; $R_5$ is —OH; $R_6$ is —OCH$_3$; and $R_7$ is —H or —OH; in ethanol in a separate container. These components are mixed thoroughly until a uniform preparation is ready A suitable amount of another polymer is added to complete the reaction. The mixture is homogenized for 10 minutes at low RPM to form a crude emulsion, and then transferred into a high pressure homogenizer. The preparation is sonicated for 20 minutes to complete the reaction and formation of nanoparticles. The resulting system is transferred into a rotary evaporator, and the organic solvent is rapidly removed at 40° C., at reduced pressure (30 mm Hg) for 20-30 minutes. The dispersion is then further lyophilized for 48 hours. The resulting cake can be easily reconstituted to the original dispersion by addition of sterile water or saline, which may contain antimicrobial agent(s).

Example 3—Bexarotene Hybrid 250 mg of bexarotene in enough amount of ethanol so that it is in solution. into 500 mg of $2^{nd}$ partner selected from the group consisting of: (a) curcumin; (b) a curcuminoid of formula (I) in which: (i) $R_1$ is —H or —OCH$_3$; $R_2$ is —OH; $R_3$ is —H; $R_4$ is H; $R_5$ is —H or OCH$_3$; $R_6$ is —OH, and $R_7$ is —H, wherein only one of $R_1$ and $R_5$ is —OCH$_3$; (ii) $R_1$ is —H; $R_2$ is —OH; $R_3$ is —H or —OH; $R_4$ is —H, $R_5$ is —H; $R_6$ is —OH; and $R_7$ is —H or —OH; (iii) each of $R_1$, $R_2$, and $R_3$ is —H, —OCH$_3$, —OH, —ONa, acetyl, methyl, or ethyl; $R_4$ is —H, —OH, ethyl, methyl, or acetyl; and each of $R_5$, $R_6$, and $R_7$ is —H, —OCH$_3$, —OH, —ONa, acetyl, methyl, or ethyl, wherein if $R_4$ is —H or —OH, at least one of $R_2$ and $R_6$ is other than —H or —OH; (iv) $R_1$ is —OH, $R_2$ is —OH, $R_3$ is —OH, $R_4$ is —H or —OH, $R_5$ is —OH, $R_6$ is —OH; and $R_7$ is —OH; (v) $R_1$ is —OCH$_3$; $R_2$ is —OCH$_3$; $R_3$ is —OCH$_3$; $R_4$ is —H or —OH; $R_5$ is —OCH$_3$; $R_6$ is —OCH$_3$; and $R_7$ is —OCH$_3$; (vi) $R_1$ is —H; $R_2$ is —OCH$_3$; $R_3$ is —OCH$_3$; $R_4$ is —H or —OH; $R_5$ is —H; $R_6$ is —OCH$_3$; and $R_7$ is —OCH$_3$; (vii) $R_1$ is —H; $R_2$ is —OH; $R_3$ is —H; $R_4$ is —H; $R_5$ is —H or —OH; $R_6$ is —OH; and $R_7$ is —H; (viii) $R_1$ is —H; $R_2$ is —OCH$_3$; $R_3$ is —H; $R_4$ is —H; $R_5$ is —H or —OH; $R_6$ is —OCH$_3$; and $R_7$ is —H; or (ix) $R_1$ is —OH; $R_2$ is —OCH$_3$; $R_3$ is —H or —OH; $R_4$ is H or —OH; $R_5$ is —OH; $R_6$ is —OCH$_3$; and $R_7$ is —H or —OH; in ethanol in a separate container. These components are mixed thoroughly until a uniform preparation is ready. A suitable amount of another polymer is added to complete the reaction. The mixture is homogenized for 10 minutes at low RPM to form a crude emulsion, and then transferred into a high pressure homogenizer. The preparation is sonicated for 20 minutes to complete the reaction and formation of nanoparticles. The resulting system is transferred into a rotary evaporator, and the organic solvent is rapidly removed at 40° C., at reduced pressure (30 mm Hg) for 20-30 minutes. The dispersion is then further lyophilized for 48 hours. The resulting cake can be easily reconstituted to the original dispersion by addition of sterile water or saline, which may contain antimicrobial agent(s).

Example 4 Camptothecin Hybrid

Water-soluble camptothecin hybrid drug is prepared to dissolve 500 mg of camptothecin into 1 gram of 2nd partner selected from the group consisting of: (a) curcumin; (b) a curcuminoid of formula (I) in which: (i) R1 is —H or —OCH3; R2 is —OH; R3 is —H; R4 is H; R5 is —H or OCH3; R6 is —OH, and R7 is —H, wherein only one of R1 and R5 is —OCH3; (ii) R1 is —H; R2 is —OH; R3 is —H or —OH; R4 is —H, R5 is —H; R6 is —OH; and R7 is —H or —OH; (iii) each of R1, R2, and R3 is —H, —OCH3, —OH, —ONa, acetyl, methyl, or ethyl; R4 is —H, —OH, ethyl, methyl, or acetyl; and each of R5, R6, and R7 is —H, —OCH3, —OH, —ONa, acetyl, methyl, or ethyl, wherein if R4 is —H or —OH, at least one of R2 and R6 is other than —H or —OH; (iv) R1 is —OH, R2 is —OH, R3 is —OH, R4 is —H or —OH, R5 is —OH, R6 is —OH; and R7 is —OH; (v) R1 is —OCH3; R2 is —OCH3; R3 is —OCH3; R4 is —H or —OH; R5 is —OCH3; R6 is —OCH3; and R7 is —OCH3; (vi) R1 is —H; R2 is —OCH3; R3 is —OCH3; R4 is —H or —OH; R5 is —H; R6 is —OCH3; and R7 is —OCH3; (vii) R1 is —H; R2 is —OH; R3 is —H; R4 is —H; R5 is —H or —OH; R6 is —OH; and R7 is —H; (viii) R1 is —H; R2 is —OCH3; R3 is —H; R4 is —H; R5 is —H or —OH; R6 is —OCH3; and R7 is —H; or (ix) R1 is —OH; R2 is —OCH3; R3 is —H or —OH; R4 is H or —OH; R5 is —OH; R6 is —OCH3; and R7 is —H or —OH; in ethanol in a separate container. These components are mixed thoroughly until a uniform preparation is ready. A suitable amount of another polymer is added to complete the reaction. The mixture is homogenized for 10 minutes at low RPM to form a crude emulsion, and then transferred into a high pressure homogenizer. The preparation is sonicated for 20 minutes to complete the reaction and formation of nanoparticles. The resulting system is transferred into a rotary evaporator, and the organic solvent is rapidly removed at 40° C., at reduced pressure (30 mm Hg) for 20-30 minutes. The dispersion is then further lyophilized for 48 hours. The resulting cake can be easily reconstituted to the original dispersion by addition of sterile water or saline, which may contain antimicrobial agent(s).

Example 5 All Trans Retinoic Acid Hybrid

Water-soluble all trans retinoic acid (ATRA) hybrid drug is prepared to dissolve 500 mg of ATRA into 1 gram of a $2^{nd}$ partner selected from the group consisting of: (a) curcumin; (b) a curcuminoid of formula (I) in which: (i) $R_1$ is —H or —OCH$_3$; $R_2$ is —OH; $R_3$ is —H; $R_4$ is H; $R_5$ is —H or $OCH_3$; $R_6$ is —OH, and $R_7$ is —H, wherein only one of $R_1$ and $R_5$ is —$OCH_3$; (ii) $R_1$ is —H; $R_2$ is —OH; $R_3$ is —H or —OH; $R_4$ is —H, $R_5$ is —H; $R_6$ is —OH; and $R_7$ is —H or —OH; (iii) each of $R_1$, $R_2$, and $R_3$ is —H, —$OCH_3$, —OH, —ONa, acetyl, methyl, or ethyl; $R_4$ is —H, —OH, ethyl, methyl, or acetyl; and each of $R_5$, $R_6$, and $R_7$ is —H, —$OCH_3$, —OH, —ONa, acetyl, methyl, or ethyl, wherein if $R_4$ is —H or —OH, at least one of $R_2$ and $R_6$ is other than —H or —OH; (iv) $R_1$ is —OH, $R_2$ is —OH, $R_3$ is —OH, $R_4$ is —H or —OH, $R_5$ is —OH, $R_6$ is —OH; and $R_7$ is —OH; (v) $R_1$ is —$OCH_3$; $R_2$ is —$OCH_3$; $R_3$ is —$OCH_3$; $R_4$ is —H or —OH; $R_5$ is —$OCH_3$; $R_6$ is —$OCH_3$; and $R_7$ is —$OCH_3$; (vi) $R_1$ is —H; $R_2$ is —$OCH_3$; $R_3$ is —$OCH_3$; $R_4$ is —H or —OH; $R_5$ is —H; $R_6$ is —$OCH_3$; and $R_7$ is —$OCH_3$; (vii) $R_1$ is —H; $R_2$ is —OH; $R_3$ is —H; $R_4$ is —H; $R_5$ is —H or —OH; $R_6$ is —OH; and $R_7$ is —H; (viii) $R_1$ is —H; $R_2$ is —$OCH_3$; $R_3$ is —H; $R_4$ is —H; $R_5$ is —H or —OH; $R_6$ is —$OCH_3$; and $R_7$ is —H; or (ix) $R_1$ is —OH; $R_2$ is —$OCH_3$; $R_3$ is —H or —OH; $R_4$ is H or —OH; $R_5$ is —OH; $R_6$ is —$OCH_3$; and $R_7$ is —H or —OH; in ethanol in a separate container. These components are mixed thoroughly until a uniform preparation is ready. A suitable amount of another polymer is added to complete the reaction. The mixture is homogenized for 10 minutes at low RPM to form a crude emulsion, and then transferred into a high pressure homogenizer. The preparation is sonicated for 20 minutes to complete the reaction and formation of nanoparticles. The resulting system is transferred into a rotary evaporator, and the organic solvent is rapidly removed at 40° C., at reduced pressure (30 mm Hg) for 20-30 minutes. The dispersion is then further lyophilized for 48 hours. The resulting cake can be easily reconstituted to the original dispersion by addition of sterile water or saline, which may contain antimicrobial agent(s).

Example 6—Acetyl Salicylic Acid Hybrid

Water-soluble acetyle salicylic acid hybrid drug is prepared to dissolve 500 mg of acetyle salicylic acid into 1 gram of $2^{nd}$ partner selected from the group consisting of: (a) curcumin; (b) a curcuminoid of formula (I) in which: (i) $R_1$ is —H or —$OCH_3$; $R_2$ is —OH; $R_3$ is —H; $R_4$ is H; $R_5$ is —H or $OCH_3$; $R_6$ is —OH, and $R_7$ is —H, wherein only one of $R_1$ and $R_5$ is —$OCH_3$; (ii) $R_1$ is —H; $R_2$ is —OH; $R_3$ is —H or —OH; $R_4$ is —H, $R_5$ is —H; $R_6$ is —OH; and $R_7$ is —H or —OH; (iii) each of $R_1$, $R_2$, and $R_3$ is —H, —$OCH_3$, —OH, —ONa, acetyl, methyl, or ethyl; $R_4$ is —H, —OH, ethyl, methyl, or acetyl; and each of $R_5$, R6, and $R_7$ is —H, —$OCH_3$, —OH, —ONa, acetyl, methyl, or ethyl, wherein if $R_4$ is —H or —OH, at least one of $R_2$ and $R_6$ is other than —H or —OH; (iv) $R_1$ is —OH, $R_2$ is —OH, $R_3$ is —OH, $R_4$ is —H or —OH, $R_5$ is —OH, $R_6$ is —OH; and $R_7$ is —OH; (v) $R_1$ is —$OCH_3$; $R_2$ is —$OCH_3$; $R_3$ is —$OCH_3$; $R_4$ is —H or —OH; $R_5$ is —$OCH_3$; $R_6$ is —$OCH_3$; and $R_7$ is —$OCH_3$; (vi) $R_1$ is —H; $R_2$ is —$OCH_3$; $R_3$ is —$OCH_3$; $R_4$ is —H or —OH; $R_5$ is —H; $R_6$ is —$OCH_3$; and $R_7$ is —$OCH_3$; (vii) $R_1$ is —H; $R_2$ is —OH; $R_3$ is —H; $R_4$ is —H; $R_5$ is —H or —OH; $R_6$ is —OH; and $R_7$ is —H; (viii) $R_1$ is —H; $R_2$ is —$OCH_3$; $R_3$ is —H; $R_4$ is —H; $R_5$ is —H or —OH; $R_6$ is —$OCH_3$; and $R_7$ is —H; or (ix) $R_1$ is —OH; $R_2$ is —$OCH_3$; $R_3$ is —H or —OH; $R_4$ is H or —OH; $R_5$ is —OH; $R_6$ is —$OCH_3$; and $R_7$ is —H or —OH; in ethanol in a separate container. These components are mixed thoroughly until a uniform preparation is ready. A suitable amount of another polymer is added to complete the reaction. The mixture is homogenized for 10 minutes at low RPM to form a crude emulsion, and then transferred into a high pressure homogenizer. The preparation is sonicated for 20 minutes to complete the reaction and formation of nanoparticles. The resulting system is transferred into a rotary evaporator, and the organic solvent is rapidly removed at 40° C., at reduced pressure (30 mm Hg) for 20-30 minutes. The dispersion is then further lyophilized for 48 hours. The resulting cake can be easily reconstituted to the original dispersion by addition of sterile water or saline, which may contain antimicrobial agent(s).

Example 7—Resveratrol Hybrid

Water-soluble Resveratrol hybrid drug is prepared to dissolve 500 mg of resveratrol into 1 gram of 2nd partner selected from the group consisting of: (a) curcumin; (b) a curcuminoid of formula (I) in which: (i) R1 is —H or —OCH3; R2 is —OH; R3 is —H; R4 is H; R5 is —H or OCH3; R6 is —OH, and R7 is —H, wherein only one of R1 and R5 is —OCH3; (ii) R1 is —H; R2 is —OH; R3 is —H or —OH; R4 is —H, R5 is —H; R6 is —OH; and R7 is —H or —OH; (iii) each of R1, R2, and R3 is —H, —OCH3, —OH, —ONa, acetyl, methyl, or ethyl; R4 is —H, —OH, ethyl, methyl, or acetyl; and each of R5, R6, and R7 is —H, —OCH3, —OH, —ONa, acetyl, methyl, or ethyl, wherein if R4 is —H or —OH, at least one of R2 and R6 is other than —H or —OH; (iv) R1 is —OH, R2 is —OH, R3 is —OH, R4 is —H or —OH, R5 is —OH, R6 is —OH; and R7 is —OH; (v) R1 is —OCH3; R2 is —OCH3; R3 is —OCH3; R4 is —H or —OH; R5 is —OCH3; R6 is —OCH3; and R7 is —OCH3; (vi) R1 is —H; R2 is —OCH3; R3 is —OCH3; R4 is —H or —OH; R5 is —H; R6 is —OCH3; and R7 is —OCH3; (vii) R1 is —H; R2 is —OH; R3 is —H; R4 is —H; R5 is —H or —OH; R6 is —OH; and R7 is —H; (viii) R1 is —H; R2 is —OCH3; R3 is —H; R4 is —H; R5 is —H or —OH; R6 is —OCH3; and R7 is —H; or (ix) R1 is —OH; R2 is —OCH3; R3 is —H or —OH; R4 is H or —OH; R5 is —OH; R6 is —OCH3; and R7 is —H or —OH; in ethanol in a separate container. These components are mixed thoroughly until a uniform preparation is ready. A suitable amount of another polymer is added to complete the reaction. The mixture is homogenized for 10 minutes at low RPM to form a crude emulsion, and then transferred into a high pressure homogenizer. The preparation is sonicated for 20 minutes to complete the reaction and formation of nanoparticles. The resulting system is transferred into a rotary evaporator, and the organic solvent is rapidly removed at 40° C., at reduced pressure (30 mm Hg) for 20-30 minutes. The dispersion is then further lyophilized for 48 hours. The resulting cake can be easily reconstituted to the original dispersion by addition of sterile water or saline, which may contain antimicrobial agent(s).

Example 8—Diazepam Hybrid

Water-soluble diazepam hybrid drug is prepared to dissolve 500 mg of diazepam into 1 gram of 2nd partner selected from the group consisting of: (a) curcumin; (b) a curcuminoid of formula (I) in which: (i) R1 is —H or —OCH3; R2 is —OH; R3 is —H; R4 is H; R5 is —H or OCH3; R6 is —OH, and R7 is —H, wherein only one of R1 and R5 is —OCH3; (ii) R1 is —H; R2 is —OH; R3 is —H or —OH; R4 is —H, R5 is —H; R6 is —OH; and R7 is —H or —OH; (iii) each of R1, R2, and R3 is —H, —OCH3, —OH, —ONa, acetyl, methyl, or ethyl; R4 is —H, —OH, ethyl, methyl, or acetyl; and each of R5, R6, and R7 is —H, —OCH3, —OH, —ONa, acetyl, methyl, or ethyl, wherein if R4 is —H or —OH, at least one of R2 and R6 is other than —H or —OH; (iv) R1 is —OH, R2 is —OH, R3 is —OH, R4 is —H or —OH, R5 is —OH, R6 is —OH; and R7 is —OH; (v) R1 is —OCH3; R2 is —OCH3; R3 is —OCH3; R4 is —H or —OH; R5 is —OCH3; R6 is —OCH3; and R7 is —OCH3; (vi) R1 is —H; R2 is —OCH3; R3 is —OCH3; R4 is —H or —OH; R5 is —H; R6 is —OCH3; and R7 is —OCH3; (vii) R1 is —H; R2 is —OH; R3 is —H; R4 is —H; R5 is —H or —OH; R6 is —OH; and R7 is —H; (viii) R1 is —H; R2 is —OCH3; R3 is —H; R4 is —H; R5 is —H or —OH; R6 is —OCH3; and R7 is —H; or (ix) R1 is —OH; R2 is —OCH3; R3 is —H or —OH; R4 is H or —OH; R5 is —OH; R6 is —OCH3; and R7 is —H or —OH; in ethanol in a separate container. These components are mixed thoroughly until a uniform preparation is ready. A suitable amount of another polymer is added to complete the reaction. The mixture is homogenized for 10 minutes at low RPM to form a crude emulsion, and then transferred into a high pressure homogenizer. The preparation is sonicated for 20 minutes to complete the reaction and formation of nanoparticles. The resulting system is transferred into a rotary evaporator, and the organic solvent is rapidly removed at 40° C., at reduced pressure (30 mm Hg) for 20-30 minutes. The dispersion is then further lyophilized for 48 hours. The resulting cake can be easily reconstituted to the original dispersion by addition of sterile water or saline, which may contain antimicrobial agent(s).

While the invention has been described in detail and with reference to specific examples thereof, it will be apparent to one skilled in the art that various changes and modifications can be made therein without departing from the spirit and scope thereof.

What is claimed is:

1. A water-solubilized hybrid drug composition comprising:
   i) a first active agent which is at least one substantially water-insoluble pharmacologically active agent, wherein said first active agent is paclitaxel;
   ii) a second agent which is at least one complementary agent, wherein the complementary agent is curcumin; and
   iii) a polymer, wherein the polymer is polyvinylpyrrolidone (PVP),
   wherein the weight ratio of paclitaxel:curcumin:polymer is 1:2:5, additionally wherein the first active agent is dissolved in an organic solvent, wherein the organic solvent is selected from the group consisting of methanol, ethanol, n-propanol, 2-propanol, n-butanol, 2-butanol, and a combination thereof, and the first active agent dissolved in an organic solvent solution is added to a solution comprising the at least one complementary agent, the polymer is added, the mixture is homogenized and sonicated, to form nanoparticles, and subject to evaporative drying, thus forming a hybrid drug composition, wherein the hybrid drug composition is water soluble,
   further wherein the composition does not comprise a surfactant.

2. A pharmaceutical composition comprising the composition of claim 1, and at least one pharmaceutically acceptable excipient.

* * * * *